US011602853B2

(12) United States Patent
Stoianovici et al.

(10) Patent No.: US 11,602,853 B2
(45) Date of Patent: Mar. 14, 2023

(54) THERAPEUTIC SOCIAL ROBOT

(71) Applicant: Colorado Seminary Which Owns and Operates the University of Denver, Denver, CO (US)

(72) Inventors: Dan Stoianovici, Denver, CO (US); Mohammad Mahoor, Lone Tree, CO (US)

(73) Assignee: University of Denver, Denver, CO (US)

(*) Notice: Subject to any disclaimer, the term of this patent is extended or adjusted under 35 U.S.C. 154(b) by 127 days.

(21) Appl. No.: 16/915,988

(22) Filed: Jun. 29, 2020

(65) Prior Publication Data

US 2020/0406468 A1    Dec. 31, 2020

Related U.S. Application Data

(60) Provisional application No. 62/868,556, filed on Jun. 28, 2019.

(51) Int. Cl.
*B25J 5/00* (2006.01)
*B25J 11/00* (2006.01)
*G16H 20/70* (2018.01)
*B25J 9/00* (2006.01)

(52) U.S. Cl.
CPC .......... *B25J 11/0005* (2013.01); *B25J 5/007* (2013.01); *B25J 9/0003* (2013.01); *G16H 20/70* (2018.01)

(58) Field of Classification Search
CPC ..... G16H 20/70; G16H 40/63; B25J 11/0005; B25J 9/0003; B25J 5/007; B25J 11/008; B25J 5/00; G06N 3/02
See application file for complete search history.

(56) References Cited

U.S. PATENT DOCUMENTS

| | | | | |
|---|---|---|---|---|
| 6,708,081 B2* | 3/2004 | Yoshida | ............ | B25J 9/161 901/1 |
| 7,047,105 B2* | 5/2006 | Kakutani | ............ | G06N 3/008 700/250 |
| 7,099,742 B2* | 8/2006 | Tajima | ............ | G06N 3/008 700/250 |
| 7,113,848 B2* | 9/2006 | Hanson | ............ | G16Z 99/00 700/258 |
| 8,909,370 B2* | 12/2014 | Stiehl | ............ | B25J 9/1671 700/264 |
| 11,026,022 B1* | 6/2021 | Tu | ............ | H04R 3/04 |
| 11,269,402 B1* | 3/2022 | Canberk | ............ | G06F 3/012 |

OTHER PUBLICATIONS

Spexard et al., Human-Oriented Interaction With an Anthropomorphic Robot, 2007, IEEE, p. 852-862 (Year: 2007).*

(Continued)

*Primary Examiner* — McDieunel Marc
(74) *Attorney, Agent, or Firm* — Neugeboren O'Dowd PC

(57) ABSTRACT

A therapeutic system comprising a posture-mimicry robot comprising a head-assembly, a neck assembly, and a body assembly comprising a hemispherical bottom portion; and a base portion comprising three rotary actuators; wherein the posture-mimicry robot is configured to perform rotational movement in each of yaw, pitch, and roll axes to perform therapeutic interactive movements, gestures, and audio-visual cues.

20 Claims, 39 Drawing Sheets

(56) References Cited

OTHER PUBLICATIONS

Hackel et al., Humanoid robot platform suitable for studying embodied interaction, 2005, IEEE, 1-6 (Year: 2005).*
Pateromichelakis et al., Head-eyes system and gaze analysis of the humanoid robot Romeo, 2014, IEEE, p. 1374-1379 (Year: 2014).*
Shamsuddin et al., Stereotyped behavior of autistic children with lower IQ level in HRI with a humanoid robot, 2013, IEEE, p. 175-180 (Year: 2013).*
Parietti et al., Independent, voluntary control of extra robotic limbs, 2017, IEEE, p. 5954-5961 (Year: 2017).*
Quick et al., Comparing the Perception of Vibrotactile Feedback across Frequency and Body Location, 2022, IEEE, p. 1-6 (Year: 2002).*
Zhang et al., An Active Neck Brace Controlled by a Joystick to Assist Head Motion, 2017, IEEE, p. 37-43 (Year: 2017).*
Kim et al., Coordinated three-dimensional motion of the head and torso by dynamic neural networks, 1998, IEEE, p. 653-666 (Year: 1998).*
Stoianovici, Dan, "NYKU: A Social Robot for Children With Autism Spectrum Disorders", Oct. 3, 2020, pp. 139, Published in: US.

* cited by examiner

THERAPEUTIC SOCIAL ROBOT

CROSS-REFERENCE TO RELATED APPLICATIONS

This application claims priority to U.S. Provisional Application No. 62/868,556, filed Jun. 28, 2019, and entitled "SOCIAL ROBOT" the entire disclosure of which is hereby incorporated by reference for all purposes.

FIELD OF THE DISCLOSURE

The present disclosure relates generally to a robot configured to convey social cues through movement, gesture, and language to facilitate therapeutic studies and treatments. In particular, but not by way of limitation, the present disclosure relates to systems, methods and apparatuses for a zoomorphic robot designed to facilitate therapy of children with autism spectrum disorder.

BACKGROUND

Robot assisted therapy (RAT) is an approach increasingly being used in the research and treatment of autism spectrum disorder, especially with children. Robots can be useful because they can provide a limited range of body language cues similar to human body language cues that can help patients learn how to interact in response to these cues. There are several existing social robots developed for RAT on the market. However, these robots range in price and quality dramatically. Some are as inexpensive as thirty dollars but lack effective therapeutic functionality. The most expensive robot available on a commercial scale has a variety of functions, but costs over $10,000 per unit. Low functionality and high cost are both barriers to widespread use and adoption by researchers and therapists. Therefore, a need exists for a social robot that can provide therapeutic functionality at a low cost.

SUMMARY

An aspect of the disclosure provides a robot comprising a head portion having a graphical display configured to display an animated representation of eyes; one or more microphones; one or more speakers; and wherein the head portion can move in a plurality of directions; a body portion having a rounded bottom, the body portion configured to perform rotational movement via omni-wheel kinematics in each of yaw, pitch, and roll axes such that the body portion leans forward, backward, and side to side; at least one arm flap portion connected to the body portion and configured to move in at least one direction in relation to the body portion; a base portion upon which the body portion having a rounded bottom sits, one or more processors; one or more motors; and one or more memories; wherein the one or more processors are programmable by an end user to instruct the robot to perform therapeutic interactive movements, gestures, and audio-visual cues.

DETAILED DESCRIPTION

The word "exemplary" is used herein to mean "serving as an example, instance, or illustration." Any embodiment described herein as "exemplary" is not necessarily to be construed as preferred or advantageous over other embodiments.

Figure 4:
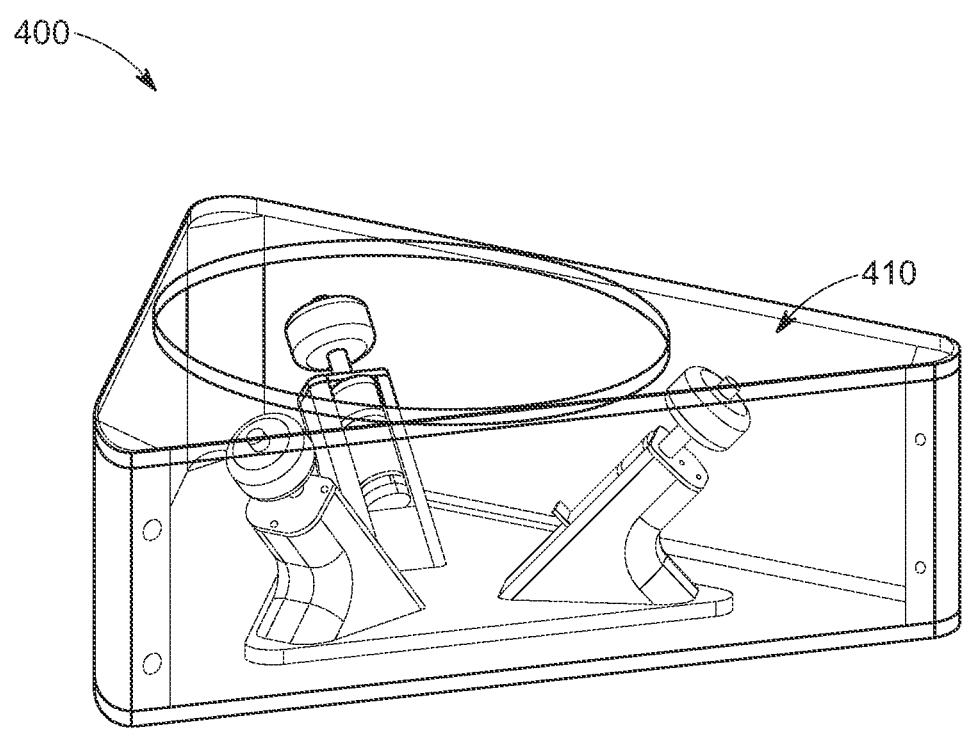
FIG. 4 shows an omni-wheel base portion of the therapeutic social robot according to an embodiment of the disclosure.
Figure 14:
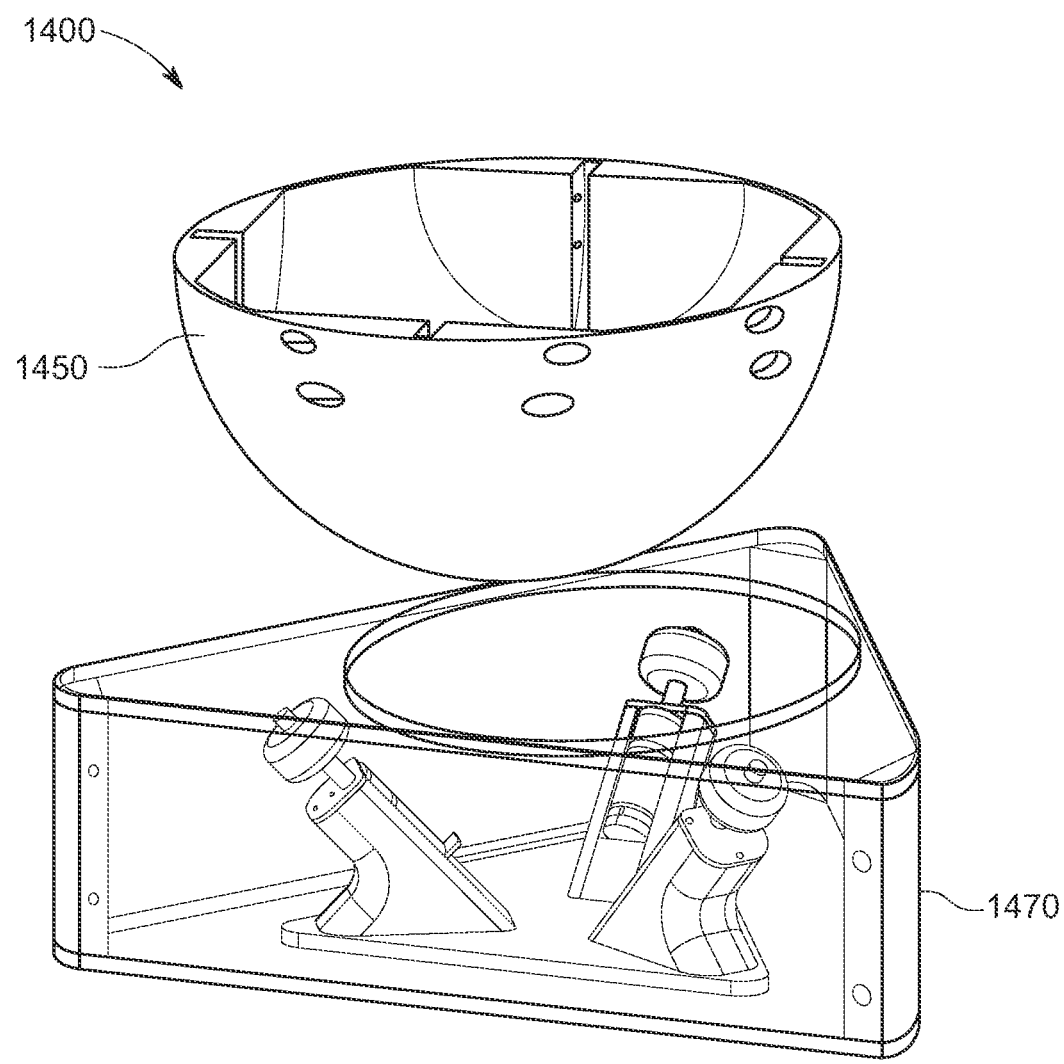
FIG. 14 shows an omni-wheel base assembly and hemispherical bottom portion of the therapeutic social robot according to an embodiment of the disclosure.

The present disclosure provides a cost-effective solution for users interested in pursuing robot assisted therapy (RAT). The social robot of the present disclosure, which many be referred to herein by its project name, Nyku, is designed to be affordable, simple to manufacture, and simple to program. Its features and overall design are configured to allow consumers and researchers alike to explore the benefits of RAT at a low cost. These components may be used to program functionality that is comparable to or exceeds that of much more expensive robots. One of the most important capabilities of any social robot is to convey "emotive actions." A unique aspect of the present disclosure is that this social robot moves its shell using omni wheels to convey these emotive actions. Specifically, an omni-wheel system may be used to have the robot lean forward and backward to convey interest, happiness, excitement, disinterest, caution, fear, and other related emotional cues. Omni-wheels are mechanical devices often used in robotics which have a plurality of discs around a wheel in various configurations. FIGS. 4, 14, and others show embodiments of the omni-wheel system, which will be described in further detail later in this disclosure.

Figure 1:
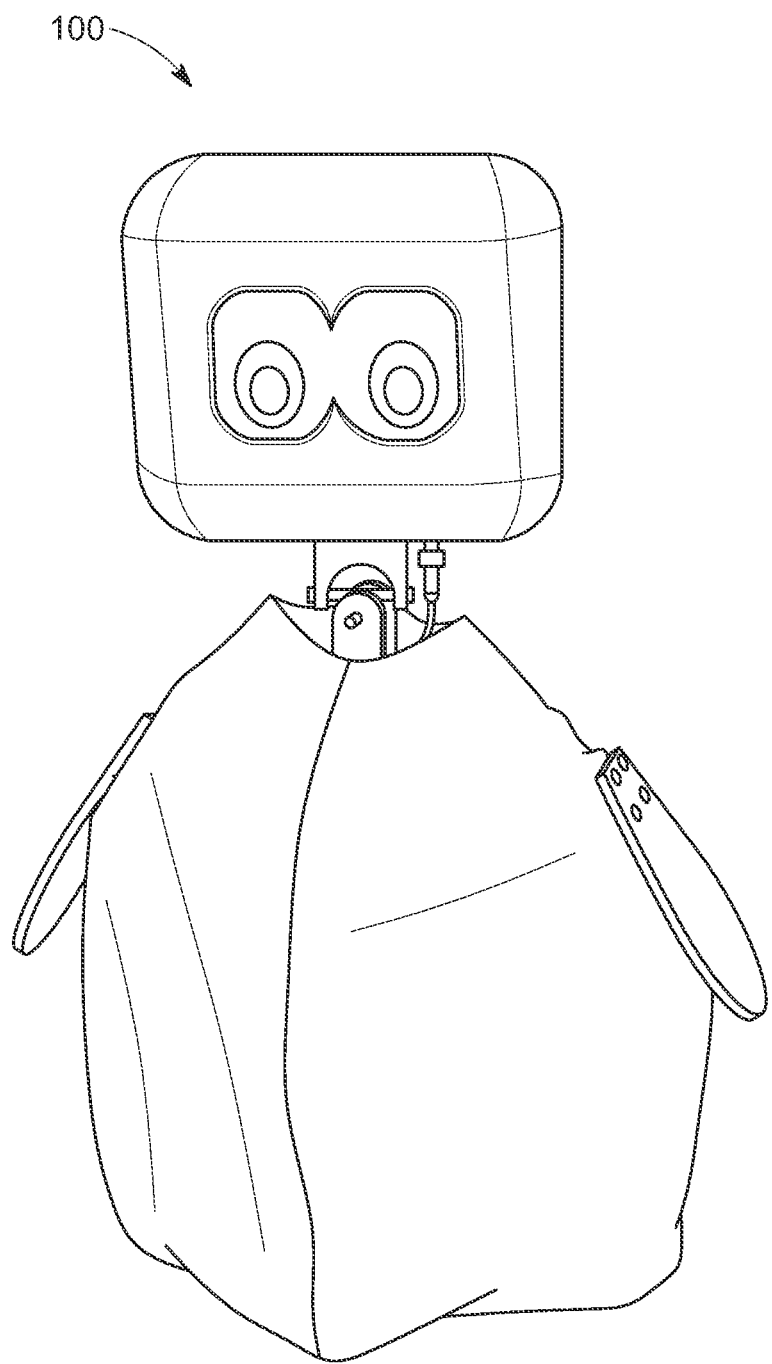
FIG. 1 shows an embodiment of a therapeutic social robot of the present disclosure.

Overview: In embodiments, the social robot of the present disclosure is implemented in a zoomorphic configuration such that it resembles a penguin. FIG. 1 shows an exemplary embodiment having a rounded, egg-shaped body, a head portion which displays big digital eyes, and flaps representing arms. The combinations of motions from the eyes, head, body, and arms may be configured to be able to display numerous kinds of emotive actions. In embodiments, the robot may be equipped with speakers and a microphone, and may be programmable to say a number of phrases in conjunction with its motions. In therapeutic sessions, the robot can convey social cues by acting as a therapist avatar, or it may perform autonomous therapeutic tasks that encourage certain behavioral responses in human patients.

FIGS. 3, 6A and 6B, and 14 show a rounded base portion of the penguin-shaped robot, which allows it to lean forward and backward via embodiments of system for controlling such leaning actions, which will be described in more detail later in the disclosure. One significant challenge to designing inexpensive robots is designing them such that they can lean in any direction without falling over.

Existing studies on autism spectrum disorder show that children with ASD have an easier time interacting with robots than traditional human therapists. Robots of this nature are proven to promote normal social interactions. This is because the children are more drawn to mechanical and predictable behaviors exhibited by robots. Children often respond better to robots because their facial expressions and other emotive actions are not as complex as those of human faces. As they become more comfortable with the interactions with the robot, they can apply these habits in interactions with their peers.

Much more research in this field is desirable, especially as it pertains to the effectiveness of robotic postures as an emotive action. Very little research has been conducted on how a robot's center of mass affects how people perceive its emotions. These studies can be implemented with the programmable social robot of the present disclosure. Because of its low cost and ease of programming, many more therapists may be able to implement it in studies of their own designs. The more studies can be conducted, the more benefits of RAT can be explored. Due to the unique mass manipulation mechanism (i.e., the systems which enables leaning in various directions without falling over), the robot of the present disclosure is able to convey ideas with its own form of body language. Such emotive actions are not available in other social robots, so the effectiveness of cues implementing posture can be further studied. The internal control system of the present disclosure enables the study of the effect of posture and associated gestures on human perception of emotion.

An additional educational benefit of the programmable robot is that it can also be used as an instructional tool for robotics labs interested in social robotics to test different forms of communication. It may also provide a platform for robotics students to learn about reaction wheels and coding with robotic operating system (ROS) in C++ and Python. Due to its ease of use, Nyku may also be accessible to consumers to enjoy as a social robot in the comfort of their own homes.

In embodiments of the social robot of the present disclosure, the head may be configured with a camera to implement object detection and control the eye gaze of the displayed eyes and/or other facial elements. It may be configured with a large digital screen to display the eyes themselves, which may move in many different directions. The head may also have an LED nose configured to blink in rhythm with speech. It may also be configured with a speaker and one or more microphones to implement communications and localize sounds for conversation. Nyku may be equipped with a natural language processing (NLP) algorithm to understand users' intention and respond to users' by having conversation or dialog with them. Nyku may be equipped with a commercially-available chatbot such as Ryan Chatbot, Program-R or PandoraBots® for conversation.

The social robot may be configured with several basic functions but may also be programmed to implement more. These functions may include those for use by a remote therapist, such as one-way video streaming, two-way audio streaming, and receiving motion controls. The robot may implement eye gaze games, such as watching a colored ball being moved from location to location, tracking objects, and using the speakers in conjunction with the eye gaze to communicate successes and failures of the game. The robot may also utilize a directional microphone to localize sounds and turn the head to make eye contact with the patient. The robot itself may implement emotive actions by leaning in various directions, moving its arm flaps, and moving its neck. Some simple functions may be implemented, such as looking at and recognizing known objects stored in a database in the computer's memory. Simple text responses may also be preprogrammed. These functions may be used to perform simple games to provide feedback to patients.

The social robot and its functions may be implemented by several components that require power supply in the form of current and voltages. These may include a computer, a motor controller and motor (e.g., a gyro flywheel), a motor/servo controller and motor (e.g., a gyro pan roll), servo controllers for the neck, an inertial mass unit, a camera, a microphone, speakers, and a screen. In some embodiments, control moment gyroscopes may be used to implement the leaning functions of the social robot. In others, reaction wheels may be used. Embodiments implementing reaction wheels will be shown and described more thoroughly in the present disclosure. In some embodiments, an omni-wheel system may be used for showing gestures. FIGS. 14-18 show embodiments of an exemplary omni-wheel system.

The omni-wheel base design shown in FIG. 14-18 uses a plurality of DC motors controlled as servos that sit at 45 degree angles in relation to a flat base. The omni-wheels attached to the motors may sit tangent to the hemisphere that is the base of Nyku social robot and allow for the hemisphere to be rotated about any axis that passes through the center of the sphere. That is, the hemisphere may rotate forward, backward, side to side, and about the vertical axis. This configuration creates a spherical joint by manipulating the outer surface of the wheel. An advantage of the omni-wheel embodiment is that it simplifies the design by allowing for positional control instead of velocity or acceleration control. This design also saves power because the weights of a gyro no longer need to spin continuously and change direction, which requires high current.

Figure 19:
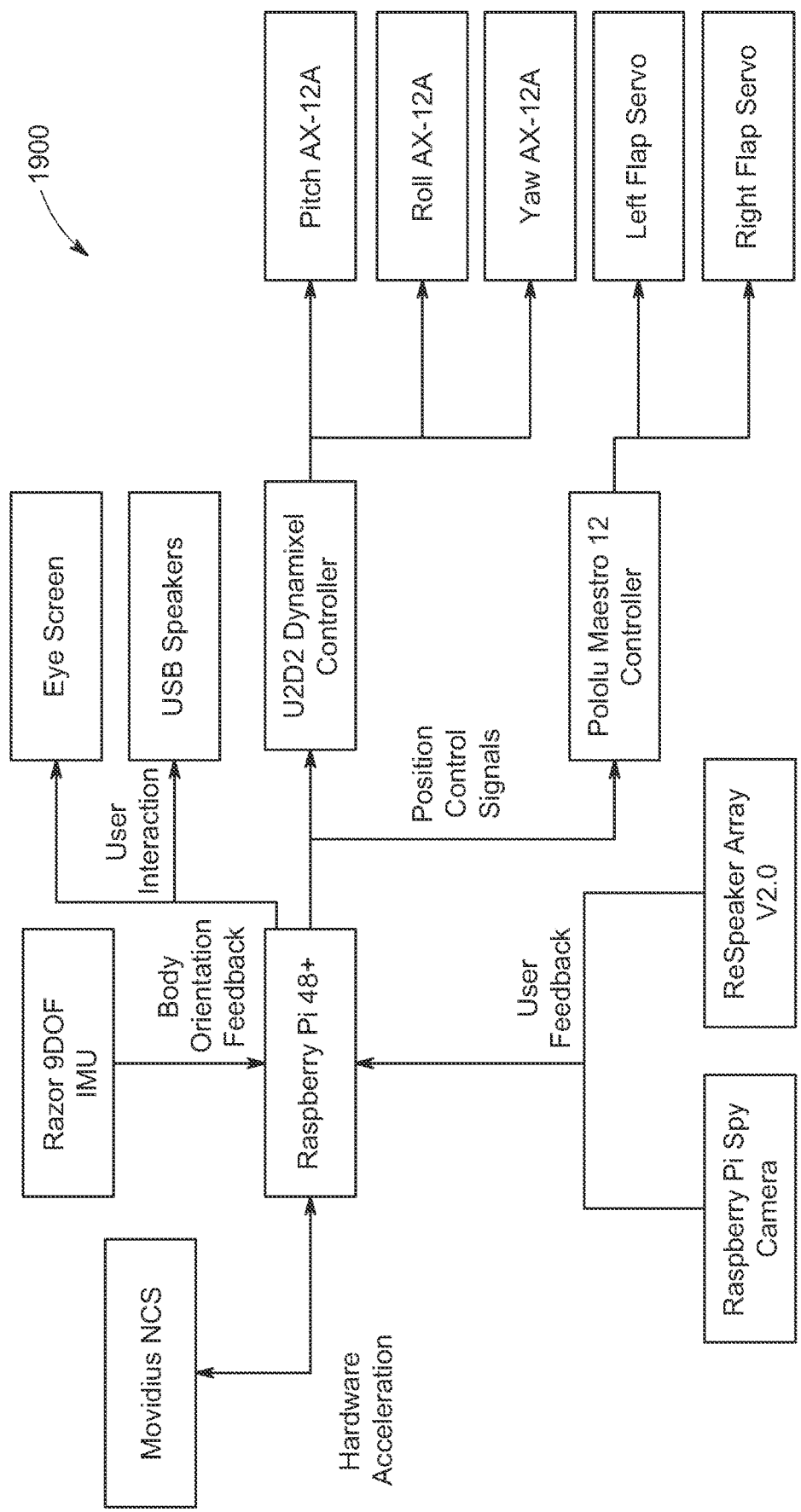
FIG. 19 is a torso control wiring diagram of components of the therapeutic social robot according to an embodiment of the disclosure.

FIG. 19 shows a logical block diagram 1900 of the overall system of the robot. Though specific types of motors and controllers are described in the figures and throughout the disclosure other types or brands of motors and controllers may be used. It is contemplated that many commercially available components of the social robot of the present disclosure may be interchanged in order to provide the lowest cost appropriate for the required functionality, ease of programming, low power consumption, and other desired attributes.

To make the social robot widely available and accessible to people with various budgets and technical programming abilities, the robot may be provided in three or more configurations. One configuration may provide just the plans, through which users could buy commercially available parts, 3D prints other components, assemble the physical components, and download the software from an open source repository. In another configuration, the robot may be provided as a disassembled kit with a portion of the components included. In another configuration, the robot may be fully assembled.

Recently, with calls for an increase in Human-Robot Interaction (HRI) studies, there has been an elevated interest in social robotics concerning the treatment of ASD children, specifically RAT for ASD children. These early studies have shown encouraging results demonstrating positive outcomes for the ASD children. In addition to this, the use of robots in therapy for children with ASD can help alleviate the well documented fatigue that occurs in ASD caretakers [8].

The lack of research in the field of Human Robot Interaction (HRI) concerning the efficacy of Robot Assisted Therapy (RAT) is caused in part by the expense of the equipment needed to conduct the research and the disconnect between Psychologists and the Engineers developing the robots. Due to this lack of research, robot assisted therapy is not commonly used in the treatment plans of ASD children, despite promising preliminary results. The recent surge in open source robotics hardware allows for the development of inexpensive robots which can be designed with very specific goals in mind. In order to expand the research horizons of RAT, inexpensive robots that meet the needs of ASD children must be designed and made easily available to those interested in conducting HRI and RAT studies.

As a burgeoning field, RAT for ASD children is showing exciting early results, however the development of the research is limited by some factors.

First, the robots used in the RAT studies are, more often than not, very costly. Most studies are conducted with NAO robots, which cost upwards of $10k for a new model, or they are purpose built robotic systems not made widely available to other research institutions. An institution interested in RAT for ASD children must therefore invest heavily in either off the shelf hardware or development costs. The issue with off the shelf hardware is that it is not built with the needs of ASD children in mind. And the issue with creating a robot for RAT is development time. The second main issue is that the robots are not designed with the all needs of ASD children in mind. For example, NAO, is marketed as a humanoid robot development platform and includes some features that may hinder its effectiveness as a therapeutic tool. Purpose built robots, on the other hand, are so specific that they only lend themselves to one specific experiment. While there are commercial robots designed for ASD children such as Keepon, their ability to accommodate a wide range of research is limited.

Given the increased interest in STEM (Science, Technology, Engineering, and Mathematics) education and the onset of the "Maker" movement, there have been a number of companies producing open source hardware for engineering development. More and more products encouraging the development of robotics are hitting the market at consumer targeted prices. Powerful microcomputers boasting 4 GB of RAM, like the Raspberry Pi 4B+ now cost around fifty dollars, and closed loop control servos can now be bought for as little as five dollars. Given this abundance of available robotics hardware, purpose built systems can be made at a reasonable price point, and the plans made available to the public. This creates the perfect environment for the development of ASD specific robots.

ASD research shows that there is much potential in studying the specific effects of body language—particularly gestures and posture—with ASD patients. Therefore, controlling the gestures and posture of a robot designed for RAT is particularly important. Each of the features and functions of the robot of the present disclosure described in detail herein have been designed to meet specific goals. The robot is designed to be capable of mimicking human body posture while serving as a remote avatar for a therapist. Overarching design criteria include 1) appealing to children with ASD, 2) not eliciting anxious behavior from the user, 2) communicate with simple non-verbal gestures, 4) mimic human body posture, 5) serve as a remote therapist, and 6) be easy and cost-effective to manufacture.

An aspect of the present disclosure provides a robot with a system having novel kinematics for the control of a sphere using a plurality of omni-wheels, which may be referred to as an "omni-wheel control system." The omni-wheel control system, its unique kinematics, and experiments conducted to validate the kinematics and the system's functionality will be discussed in thorough detail throughout the disclosure.

FIG. 1 shows an embodiment of the social robot 100 of the present disclosure. A concern of the robot is to avoid the over stimulus of the child with ASD. This over stimulus can occur if there are more methods of NVC (non-verbal communication) conveyed than can be interpreted by the ASD child. This over stimulus can overwhelm the child and reduce the therapeutic benefits of the robot. To ameliorate this problem, the Nyku has been designed with simplified NVC in mind. The two main methods of non-verbal communication come from the face, through expression, and from the body, through posture. To simplify the face based NVCs, Nyku is designed without a mouth, leaving only eye expression which can be coded to display the NVC.

Figure 2:
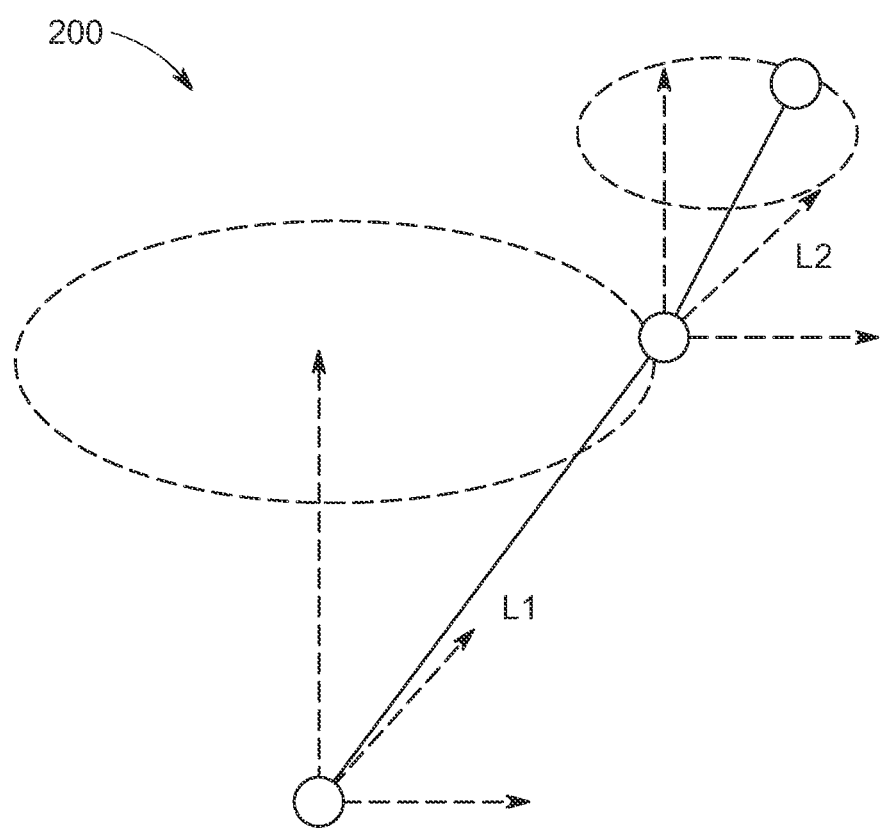
FIG. 2 is a diagram illustrating a three dimensional plane in which components of the therapeutic social robot may move.
Figure 3:
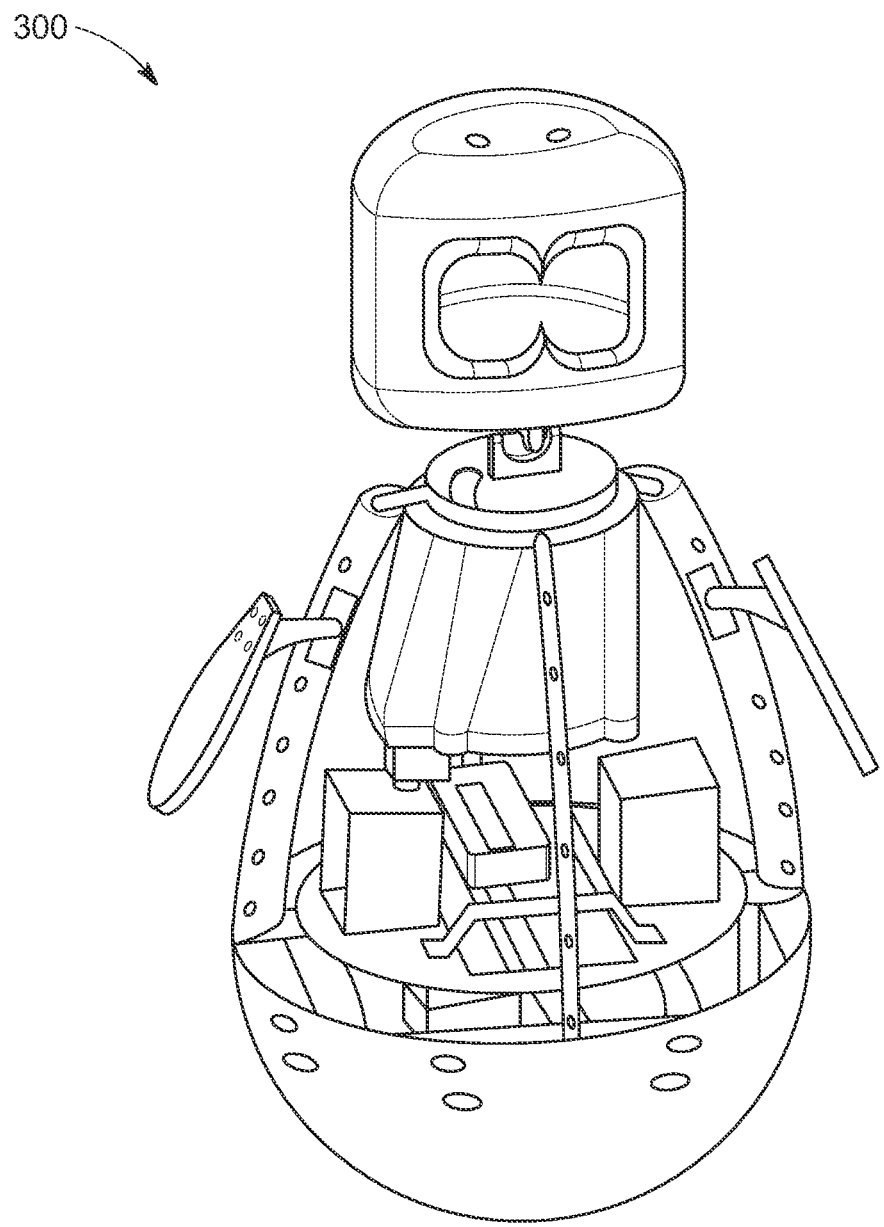
FIG. 3 shows a torso and neck assembly portion of the therapeutic social robot according to an embodiment of the disclosure.

To simplify the posture NVC from Nyku, the design models the penguin body with three links connected with two spherical joints: the inertial base link, body link, and head link. The body link also comprises two independently actuated "flippers" to achieve anatomical resemblance to a real penguin. These serve a dual purpose of allowing Nyku to more easily express more animated emotions such as excitement or surprise. Each of the body links has 3 DOF (degrees of freedom), as shown in FIG. 2, with a range capable of more that the human body so that it can exaggerate postures if necessary to dramatically convey emotions to the children. In FIG. 2, L1 represents Nyku's body link, and L2 represents the head link, the inertial link is omitted from the diagram for simplicity. The position of these two links controls Nyku' posture.

In order to act as a remote therapist, Nyku needs to be able to relay communications between therapist and patient. To accomplish this, embodiments include a camera, speakers, and a microphone. Using these tools, the therapist can hear and see the child, and the child can hear the therapist. While acting as a remote therapist, Nyku may also have to maintain eye contact and posture mimicry. This is achieved through the internal camera which can center the patients gaze and an external camera that allows for the use of deep neural networks to detect the patient's body posture. With these tools, the therapist can focus on the patient and not the control of the robot.

The design methodology of Nyku has been to simplify mechanical construction and use open source electronics in order to make the robot easy to reproduce in house. Nyku may be produced using only a large format 3D printer and a laser cutter.

Mechanical Design Overview

Using the overall design goals, technical specifications are now considered so that these goals can be achieved. The overall mechanical design of the robot is presented here. The system comprises two main parts: Nyku's torso 300, shown in FIG. 3, and the Omni-Wheel Base 400 upon which it sits, shown in FIG. 4. The torso contains links L1 and L2, as shown by FIG. 2, the body and head, which remain untethered from the Omni-Wheel base allowing for full mobility of the links. The two link system mandates that there are two joints. These roles are fulfilled by the Omni-wheel Base, which connects the torso (L1 & L2) to the inertial ground link, and the neck, which connects the body (L1) to the head (L2). In this section we present the mechanical design of these components.

The body may house all of the components for Nyku's functionality and provide interfaces for the base and neck joints. In the body of the robot, the main computer, a Raspberry Pi 4B+, as well as the peripheral controllers for the neck and the flippers are housed. The body also houses the power supply for the untethered system. Using a staged layer method we are able to separate power supply and electronics into 3 distinct layers in the body. By isolating the control and power hardware, rapid iteration of the base structure was made possible.

Figure 5A:
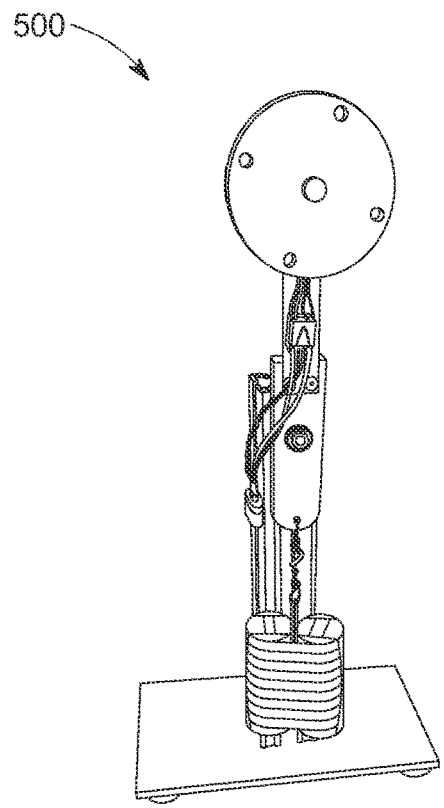
FIG. 5A shows an internal mass control system for controlling movement of a robot according to an embodiment of the disclosure.

FIG. 5A shows an embodiment of a reaction wheel internal mass control system 500 of an embodiment for controlling leaning of the robot in the present disclosure, which is an alternative to the omni-wheel control system discussed throughout the disclosure. In some embodiments, the robot may implement three reaction wheel internal mass control systems: one each to control roll, pitch, and yaw. That is, the reaction wheel systems may control the leaning side to side, leaning back and forth, and rotating motions. It is contemplated that the reaction wheel mechanism that controls the yaw (rotating about the vertical axis) may be substantially smaller than the mechanisms that control the roll and pitch because the inertia about that axis is smaller than the inertia for pitch and roll. The reaction wheel mechanism applies force to the body by accelerating and decelerating the wheel.

Figure 5B:
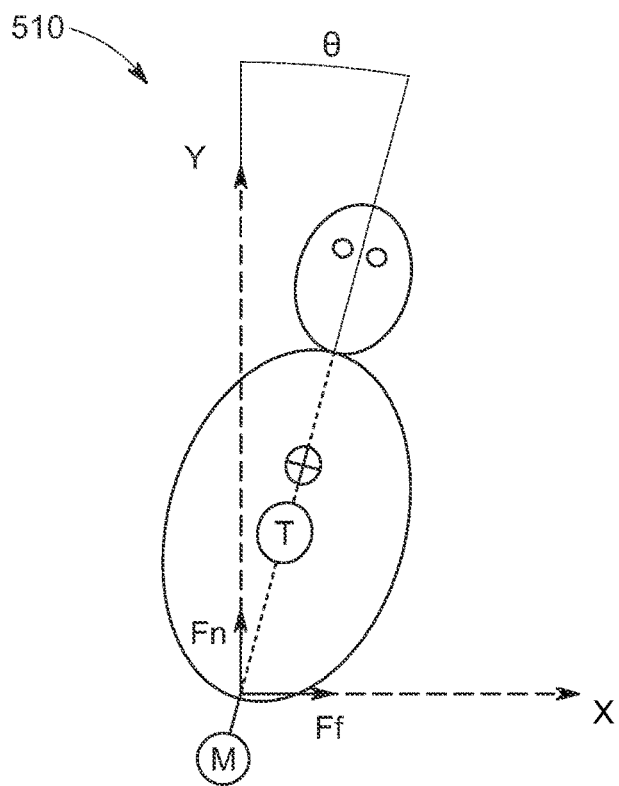
FIG. 5B is a mass control diagram illustrating aspects of the mass control system in FIG. 5A.

FIG. 5B is a force body diagram 510. The mass M represents a stable equilibrium, but contributes to the center of mass. The diagram shows, in one dimension, the torque generator T. By applying angular momentum, the reaction wheel can accelerate, the system can apply a brake to it to generate a controlled lean. The setup of the robot body allows frictional force at the bottom to overcome the angular acceleration and get to neutral so the starter doesn't have to run constantly. This allows the overall system to save battery power, and limit noise, which can be beneficial in not distracting the patient.

In order to lean, the angular momentum of the reaction wheel must be greater than the inertia of the robot plus the acceleration of the desired lean angle plus the torque caused by the action of tipping over. In order to reach a stable equilibrium where the motor does not have to be run constantly, a mass may be placed toward the bottom of the reaction wheel mechanism to lower the overall center of mass. Where the torque generated by the wheel is equal to its inertia, that generates the angular acceleration.

In embodiments the braking mechanism may feed energy back into the battery, which provides a benefit of extending battery life. By braking the reaction wheel in a precise manner, the system can very accurately position the center of mass over the tipping point of the robot. With the bottom of the robot being rounded, this accurate positioning allows more complex movements like having the head moving independently, allowing it to pitch forward while robot tilts backward, for example.

The description in the following section of the disclosure refers primarily to embodiments using the omni-wheel control system design for controlling the posture of the social robot.

Figure 6A:
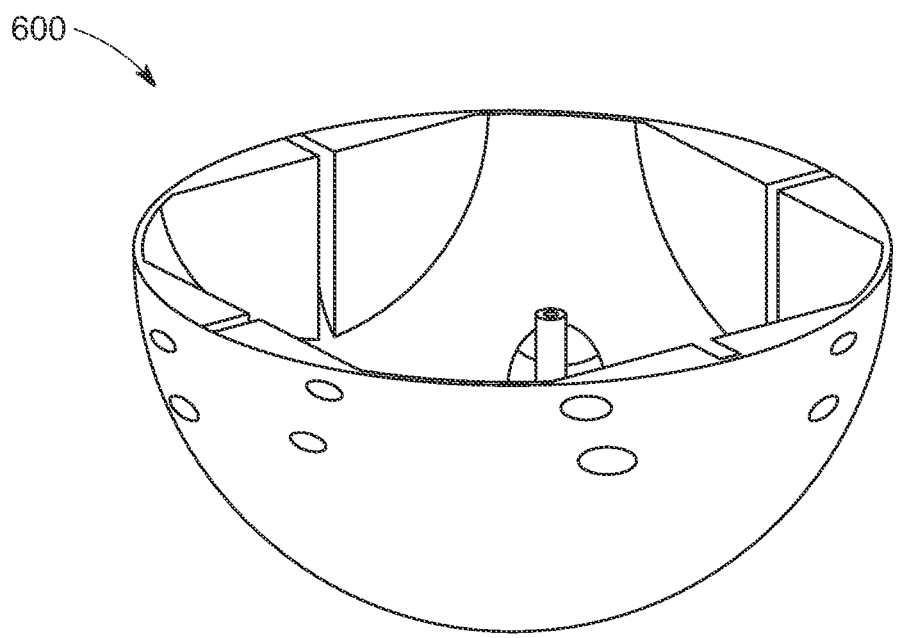
FIGS. 6A and 6B show a rounded bottom hemisphere portion of the therapeutic social robot according to an embodiment of the disclosure.
Figure 6B:
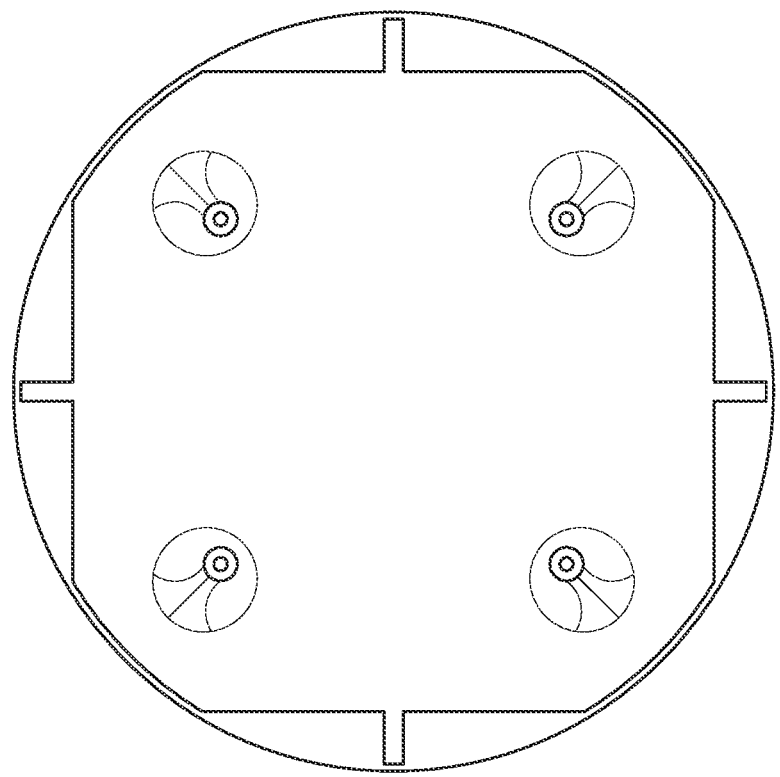
Figure 7:
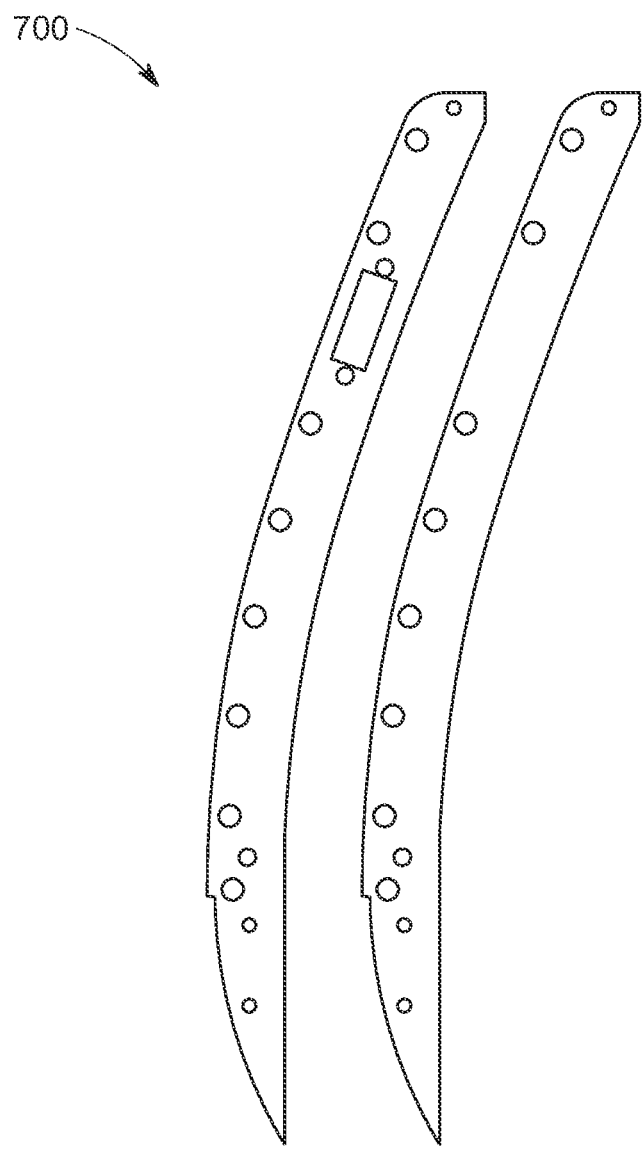
FIG. 7 shows horizontal ribs for mounting components of the therapeutic social robot according to an embodiment of the disclosure.

FIGS. 6A and 6B shows views of a hemispherical bottom 600 of the social robot. The 12 inch diameter hemispherical bottom 600 of the body is the interface between the Omni-wheel base, as well as the structural element supporting the vertical ribs. On the sides of the hemisphere there are holes that form a chord passing through the interface slits for the vertical ribs 700, visible in FIG. 7. These holes are tapered to aid in the insertion of hardware. One side of the hole is a hex fitted to a 6-32 thread hex nut for each of assembly, while the other side is circular, accommodating the 1.5" 6-32 screw itself. From the top, there are four vertical slits that house the ribs. The ribs themselves provide mounting points for the hardware layers and at the top they are connected by the neck mechanism, which will be covered in the following section.

The ribs are both a structural and aesthetic element of the design. As mentioned, they are used for structural support of the internal hardware, but they also lend to the oval shape of the robot, making Nyku look like a penguin. There are two configurations of the vertical ribs 700, both with and without the mounting holes for the servos that actuate the flippers, shown in FIG. 7. The vertical ribs also provide an interface for the horizontal ribs of the robot which define the round shape of the body. These horizontal ribs are made of 0.25" PTFE tubing. Using this material allows Nyku to have a pliable outer texture to facilitate a nice tactile sensation desirable in toys.

Figure 8:
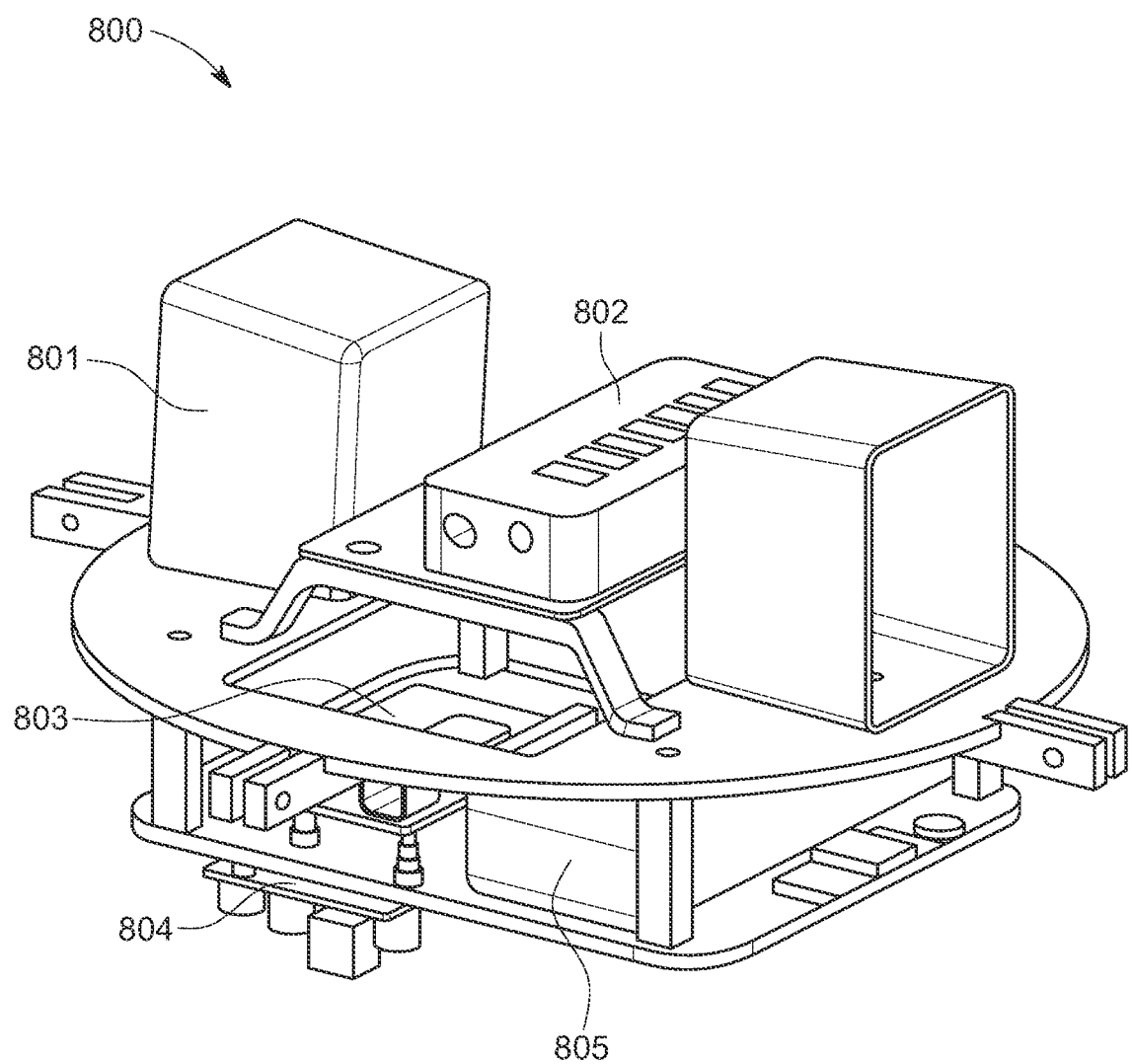
FIG. 8 shows a hardware layer comprising processors, speakers, batteries, and other components of the therapeutic social robot according to an embodiment of the disclosure.

The hardware layer 800, shown in FIG. 8, comprises the power supply for the untethered system and the control hardware for the neck and head. This layer comprises two stages, on the top stage there is a powered USB 3 hub 802 which provides power and data communication for Nyku's peripherals such as the microphone, speakers (such as USB speakers 801), screen for the eyes, communication hub for the Dynamixel servos. Dynamixel is a commercially-available brand of servos. Throughout the disclosure, various commercially-available components may be referred to by their brand names, as they are known thereunder to those of skill in the art. The social robot's speakers are also mounted upon the hardware layer. The bottom stage houses the battery 805, the Raspberry Pi 803 (a commercially available component) and Maestro Servo controller (another commercially-available component) for the flaps as well as the power supply circuit 804, which will be discussed in the electrical design section.

Above the torso a neck mechanism is situated. This mechanism serves as the joint between the body link and the head link, L1 and L2, and as such should meet certain requirements. In particular, it should withstand the loads of the heads motion and do so in a way that facilitates smooth motion. The structure should be rigid to the dynamic loads of motion and the controlling motors must not approach their maximum dynamic torque when accelerating the head.

In various embodiments, versions have a universal joint allowing for pitch and roll, and they sit on top of the yaw axis. In one embodiment, control motors may be common hobby servos which may reduce cost and allow for easy control.

Figure 9:
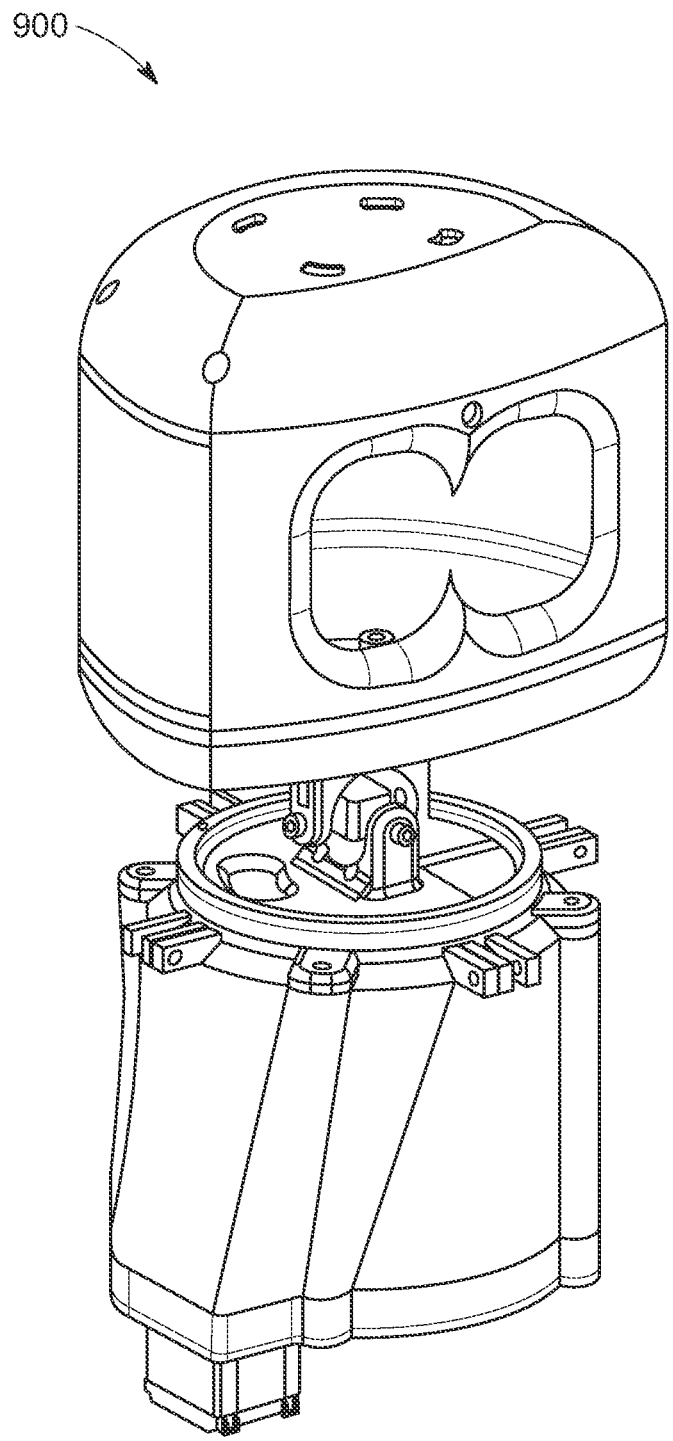
FIG. 9 shows a head and neck assembly portion of the therapeutic social robot according to an embodiment of the disclosure.
Figure 10:
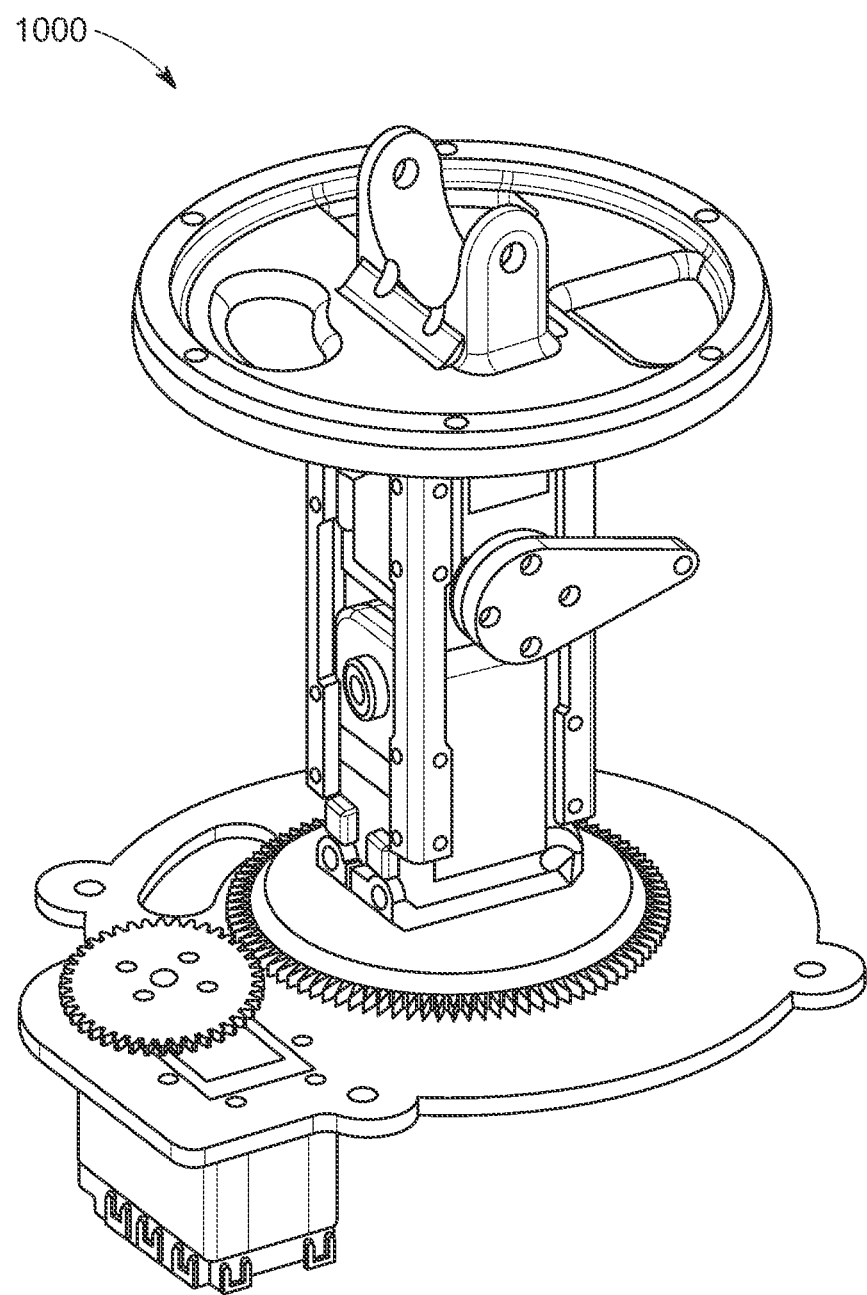
FIG. 10 shows a neck control shaft assembly of the therapeutic social robot according to an embodiment of the disclosure.

FIG. 9 shows a neck and head assembly 900. This is a modular design which bolts to the top of the ribs and holds them together solidifying Nyku's structure. The neck mechanism is designed this way in the event that the body shape needs changing. It is a fully contained system which houses 3 Dynamixel AX-12A servos for decoupled control of the roll, pitch, and yaw of the neck. The neck comprises a bottom plate, which offsets the yaw servo from the rotating shaft of the neck, via the gear train visible in FIG. 10 This is done to isolate the yaw servo from the axial load of the necks weight, and the radial load of the necks motion. Instead, the vertical shaft of the neck is constrained in the bottom plate by two bearings of different sizes. The vertical shaft itself is assembled from the two Dynamixel servos end to end. This allows the axis for roll, pitch, and yaw to intersect which aids in realistic motion of the head as well as simplifying the orientation control of the head as shown in FIG. 10.

Figure 11:
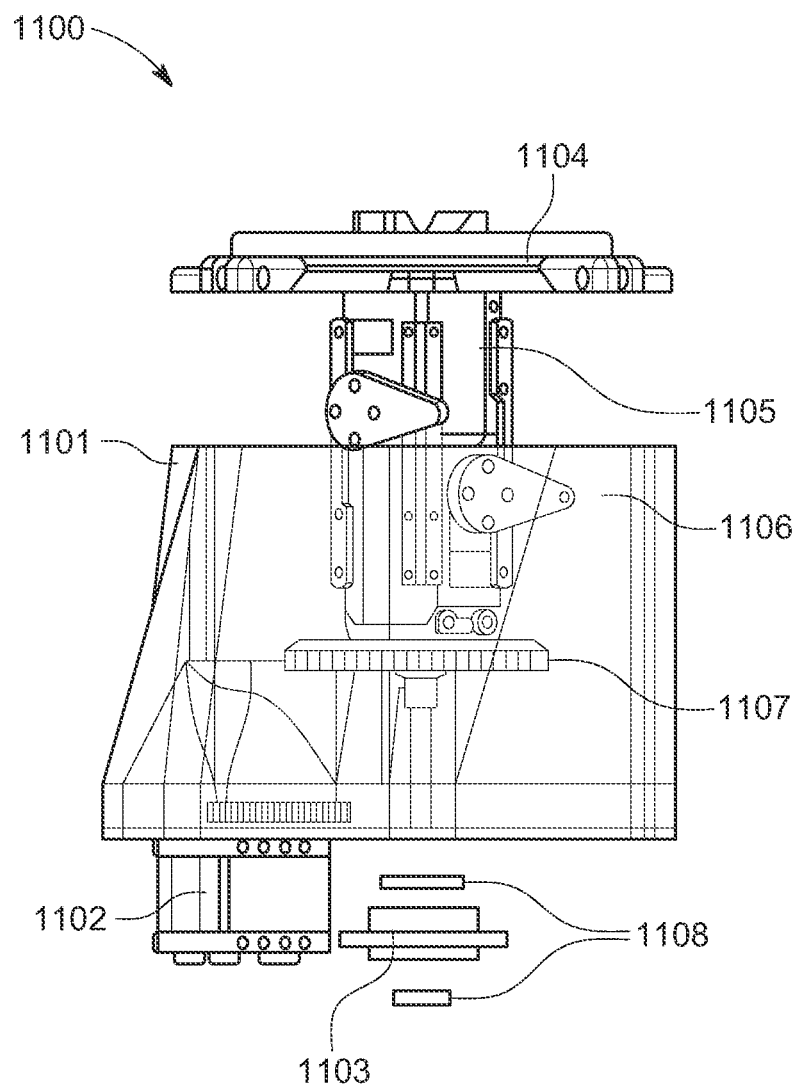
FIG. 11 shows an exploded view of the neck control assembly of FIG. 10.

In embodiments, the links may be made from 6-32 threaded shaft connected to spherical joint heads that allow the length to be tweaked by unthreading and threading on the shaft. Links are therefore measured from the SW model and tuned by hand. As seen in FIG. 10, the neck shaft 1000 is a modular unit containing both bearing interfaces and creating a module that can be disassembled without having to remove the control rods. This module is housed within a cowl that forms the outer shell of the Neck & Head module. This housing serves as an interface to tension the bearings that constrain the bottom of the Neck Control Shaft, which is shown in FIG. 11. The housing also serves to quiet the pitch and roll servos during operation for a cleaner user experience.

To constrain the top of the Neck Control Shaft, there is a bearing plate system 1104, also highlighted in FIG. 11. This comprises an upper and lower race filled with loose 5 mm steel ball bearings which are compressed by tightening the lower compression bearings. This mechanism is similar to how the headset on a bicycle works. The upper race of the bearing plate has cutouts to allow for the roll and pitch control rods, as well as the wiring for components mounted in the head. The neck control shaft 1100 further comprises a housing 1101, an AX-12A Yaw 1102, a bearing seat 1103, an AX-12A Pitch and Roll 1105, a servo horn 1106, a yaw-driven gear 1107, and upper and lower compression bearings 1108.

Figure 12:
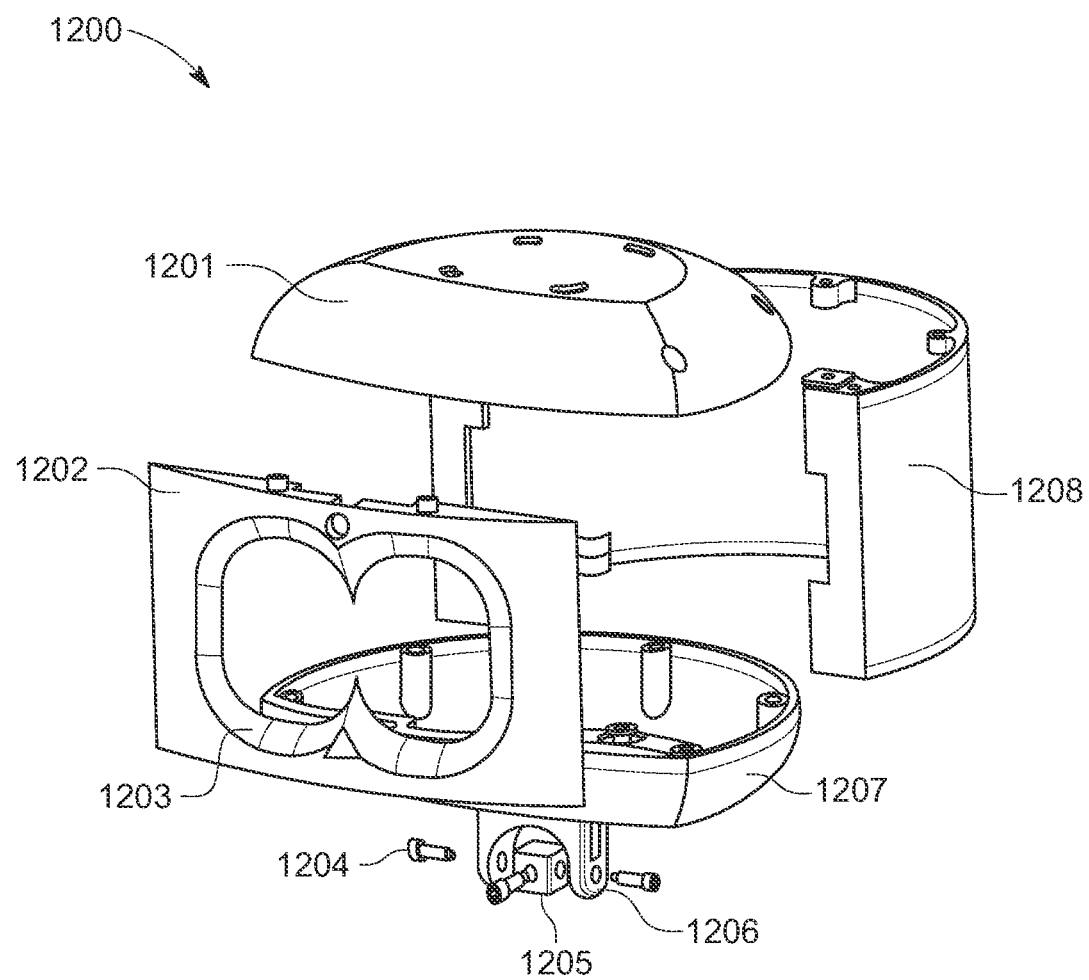
FIG. 12 shows an exploded view of the head assembly portion shown in
FIG. 9.

The head 1200 itself sits on a 3D printed U-joint atop the bearing plate, as shown in FIG. 12. This 3D printed u-joint has bearings pressed into the four side walls of the cube, which are compressed together by M4 dog-nose screws 1204 which when tightened into the heated thread inserts form the axles of the u-joint 1205. This can be seen in FIG. 12. The head itself provides an aesthetic housing for the screen used to display the eyes, the microphone to listen to the subject, and the LED 1203 for the nose, the head 1200 further comprises a top shell 1201, a face plate 1202, a housing 1208, a lower shell 1207, and an M4 heat thread insert 1206.

Figure 13A:
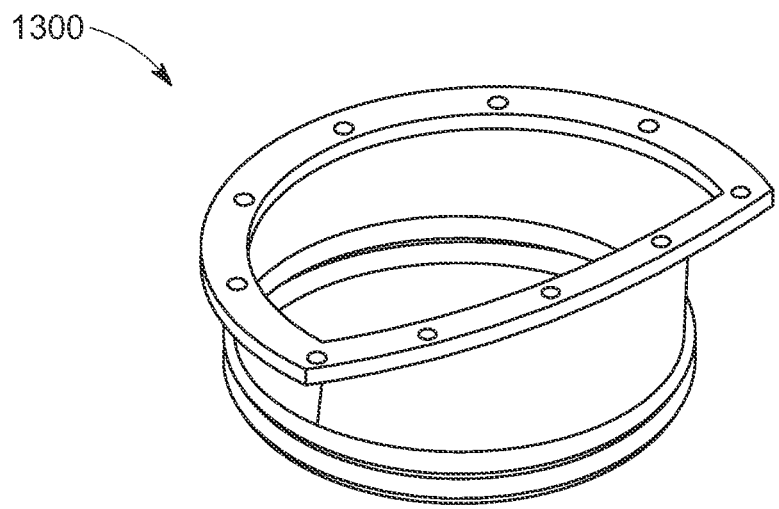
FIGS. 13A and 13B show portions of neck bellows of the therapeutic social robot according to an embodiment of the disclosure.
Figure 13B:
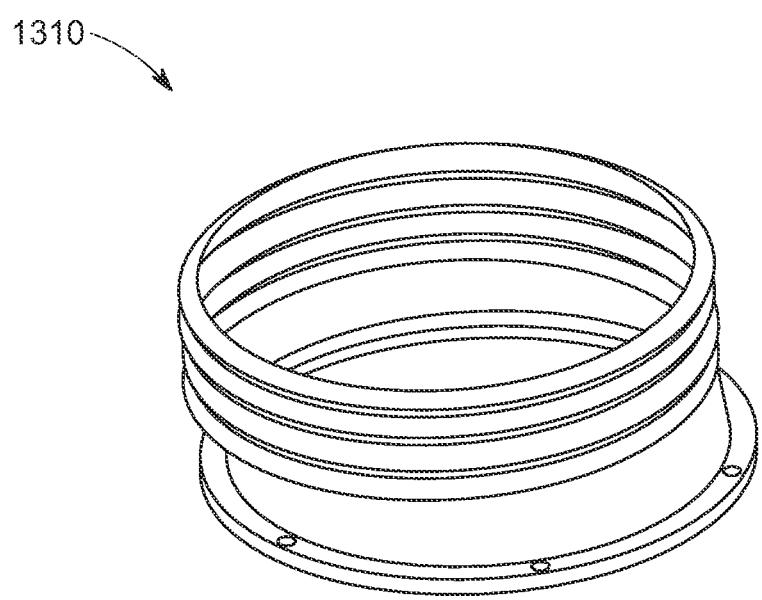

In order to achieve the aesthetic goals of the design, the neck mechanism may be covered in a flexible rubber bellows printed in TPU, as shown in FIGS. 13A and 13B. The top neck bellow 1300, in 13A, bolts to the bottom of the head, and the bottom neck bellow 1310, in 13B, bolts to the top of the bearing plate. Together, these flexible bellows overlap and cover the control rods of the neck, the u-joint mechanism, and the wiring for the head components, thus preserving the penguin aesthetic.

Omni-Wheel Base

The Omni-wheel base is the interface between Nyku's torso, L1, and the inertial link of the system, as shown in FIG. 2. This spherical joint is created by interfacing a hemisphere with 3 omni-wheels sitting tangentially on its surface. Using this configuration, the joint is able to perform infinite rotations about any axis passing through the center of the sphere. In the case of Nyku, these rotations are only limited by the hemisphere that makes up bottom of the torso.

FIG. 14 shows the hemisphere 1450 elevated from Omni-wheel Base 1470 to illustrate how the interface works. The three servos support the hemisphere at the 45° tangency point on the sphere. When the robot is placed on this interface, it flexes the acrylic bottom layer and can decrease the elevation angle of the omni-wheel servos. To alleviate this an aluminum reinforcement is bolted in between the acrylic bottom plate and the servo assemblies. This helps to preserve the kinematic model of the system used in control.

Figure 15:
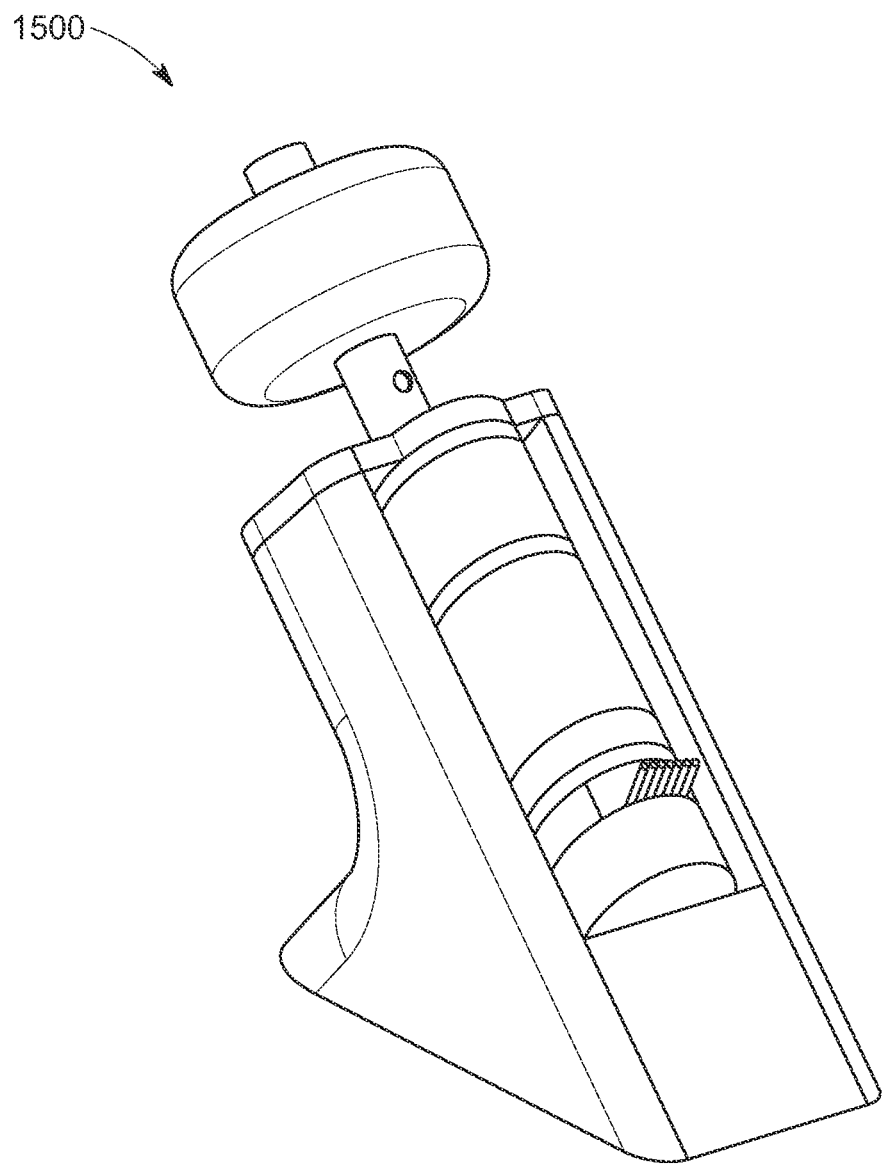
FIG. 15 shows an omni-wheel servo portion of the omni-wheel base of the present disclosure.

FIG. 15 shows an exemplary omni-wheel servo 1500, are constructed using commercially-available motors (e.g., encoded Pololu Gear Motor #4867). These are constrained using the 3D printed mounts, which set the elevation angle and bolt into the acrylic base to form the radial spacing. Using encoders for the feedback allows for a cleaner omni-wheel servo overall, and allows for automated zeroing of the body, because the IMU can be used for orientation measurement and the encoders can be reset correspondingly.

Figure 16:
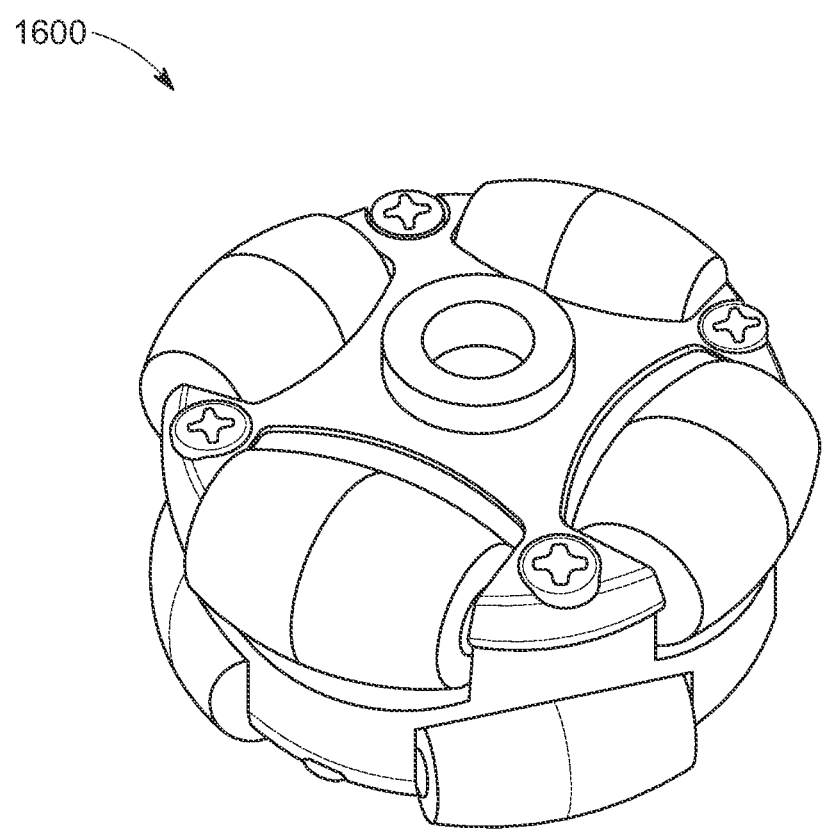
FIG. 16 shows an omni-wheel that may be used in embodiments of the present disclosure.
Figure 17:
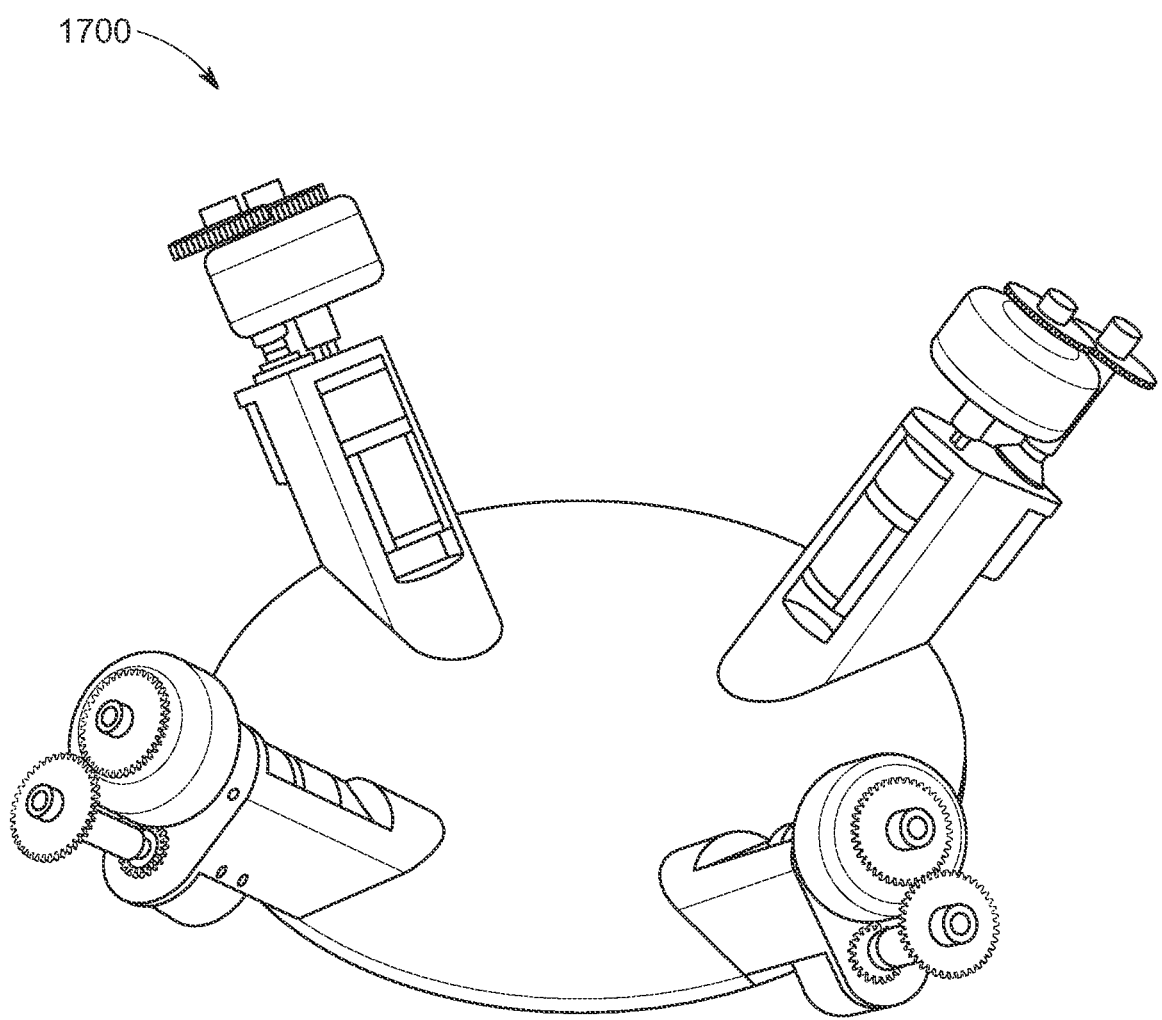
FIG. 17 shows a top perspective view of omni-wheel servos within an omni-wheel base plate of the present disclosure.
Figure 18:
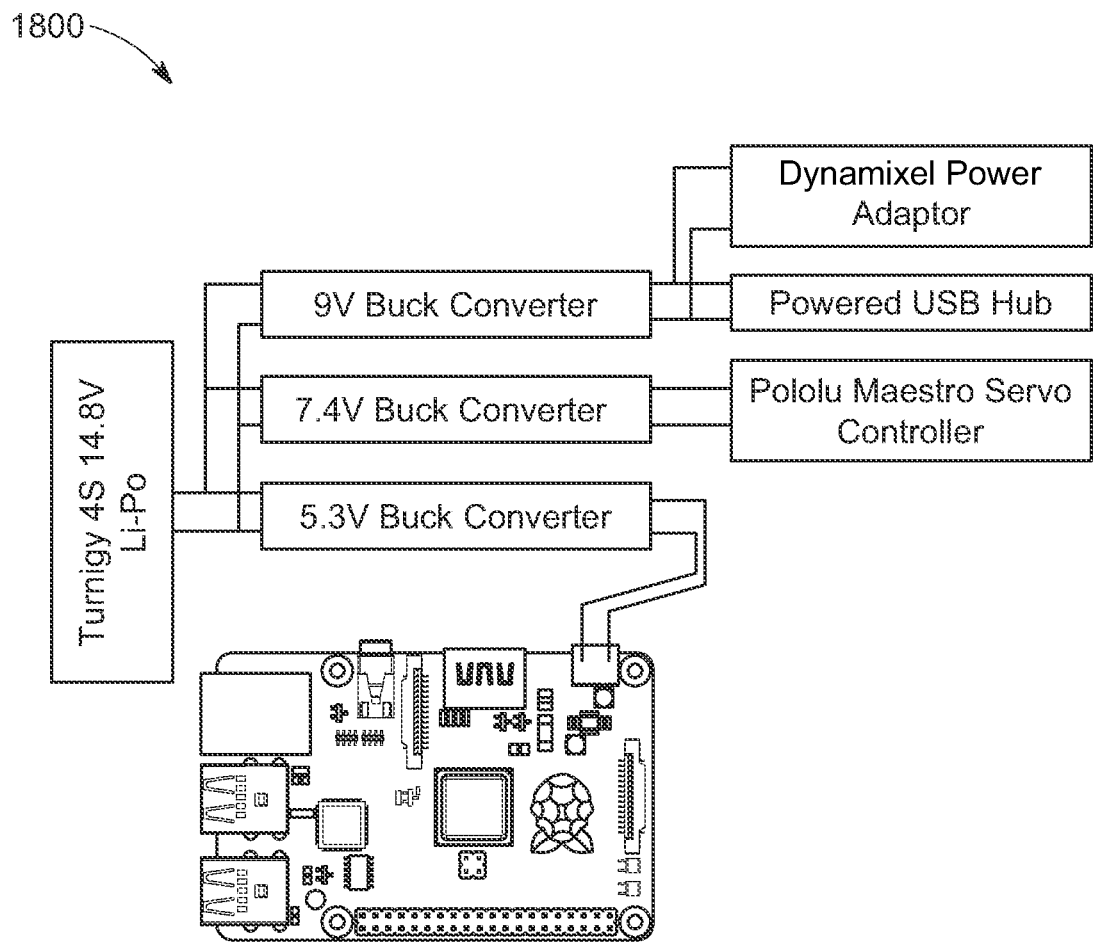
FIG. 18 is a power supply diagram of components of the therapeutic social robot according to an embodiment of the disclosure.

Mounted to the Pololu motor, are the omni wheels 1600 themselves, pictured in FIG. 16. The omni-wheels 1600 themselves are mounted to the D-shaft of the motor via set screw. These wheels have an outer diameter of 38 mm. Given the diameter of the hemisphere, in FIGS. 6A and 6B, is 12 inches, the gear ratio between the omni-wheel servo and the base is approximately 8. Using this gear ratio, the rotations of the omni-wheel servo can be mapped to an axis that is coincident with the center of the hemisphere. FIG. 17 shows a, omni-wheel servo assembly 1700 having four omni-wheel servos. The omni-wheel base 400 as shown in FIG. 4 comprises the omni-wheel servo assembly 1700 inside the triangular acrylic housing 410. This may prevent any pinch zones and creates a cleaner look. The Body, Neck & Head, and Omni-wheel Base assemblies comprise the major components in the Nyku system of the present disclosure.

Electrical Design Overview

In order to make use of the hardware included in Nyku's design, the system may be wired for control and power. In embodiments, the decoupled system architecture provides that Nyku and its Omni-Wheel base have different power supplies and control circuitry. First, the power supply of the torso will be outlined, followed by the circuits connecting the subsystems within the torso. Next, the motor control unit and its power supply will be outlined for the Omni-wheel base.

Torso Electronics: For the Torso to be a standalone unit, disconnected entirely from the Omni-wheel Base, the system may be battery powered. To achieve this, a Li—Po battery may be used to power the system. Due to the relatively long run times required, an hour, and the power draw of the system, a 4 Cell 14.8V 6.6 Ah battery was selected. From here, the power supply circuit is split into parallel loops for the necessary component voltages, as seen in the torso electronics wiring diagram 1800 of FIG. 18. The components branch off from the battery passing through a 10 Amp power switch that serves as the main power switch for the torso system. Some components are USB powered, such as the screen for the head and the speakers. These systems are connected to the powered USB hub running off of the 9V buck converter, which has maximum current higher current rating. This 9V circuit also powers the Dynamixel servos, which are the main power draw of the torso system outside of the RPi computer.

Most systems in the torso are connected via USB which also provides power. Systems like the microphone and the Movidius Neural compute stick that perform computation are connected directly to the RPi via the USB 3.0 ports to eliminate possible communication bottlenecks.

FIG. 19 shows a logical block diagram 1900 of the data connections to the torso hardware. In the embodiment shown, the RPi 4B+ is the central computer running the master ROS node. This connects to the IMU and U2D2 controller via USB2.0 and interfaces through a ROS Serial protocol. The U2D2 controller then interfaces with the AX-12A Dynamixel Servos and the power adaptor through its proprietary 3 pin connectors. The Pololu Maestro is also connected via USB through the hub and control is done through a Python interface. The USB speakers and Eye screen are powered through the USB hub but communicated with through standard 3.5 mm Jack and HDMI respectively. The spy camera connects directly to the DPI camera port on the Raspberry Pi, while the ReSpeaker Array (a commercially available component) connected via USB3.0 directly to the RPi. Because the ReSpeaker is a micro-controller that performs direction of arrival and speech detection calculations on board, this system may have rapid communication to the RPi. The Maestro controller, provides a 3 pin DuPont interface standard to hobby servo connections, where the left and right flap servos are connected. These servos, HiTech HS-5087MH, (a commercially available component) have an upper limit of 7.4V and are powered directly from the Maestro Controller which is therefore is powered from the 7.4V source as seen in FIG. 19. This details the wiring present in the torso which allows for the control of the individual system parts. Because this system is untethered, the power draw is tested under certain operating conditions so that total run-time can be more accurately predicted. Testing is conducted by measuring the max current drawn from a power supply under certain operating conditions and the amp hour rating of the battery is used to estimate the total run-time. For conditions including stall currents for motors, the stall current is added to the measured idle for the calculation. This data is presented in Table 3.1 below:

TABLE 3.1

Run-times Calculated based on 6.6 Ah battery

| Condition | Amps | Run-time (Min) |
|---|---|---|
| System Idle | 0.56 | 707.14 |
| Movidius Obj D | 0.79 | 501.2 |
| Eye display and Object Detection | 0.82 | 483.9 |
| Speech, Obj D, Eyes | 0.85 | 465.8 |
| Speech, Obj D, Eyes, Motors IDLE | 1.33 | 297.7 |
| Speech, Obj D, Eyes, Motors STALL | 7.05 | 56.1 |

As seen in Table 3.1, even at the worst case scenario where all motors, Dynamixels and servos, are stalled, the system is able to run for 56 minutes. Because this stall condition is very unlikely to occur, it is safe to assume that robot will be able to run for at least an hour long therapy session.

Omni-Wheel Base Electronics:

As discussed, the Torso may be an untethered system, while the Omni-wheel Base may not be. As such, the base has a traditional power supply, converting outlet AC to 12V DC at a maximum of 15 A. This power supply is indeed very simple as it only provides direct 12V power to the motor driver and the RPi and as such only uses one buck converter to create a 5V rail powering the RPi.

Figure 20:
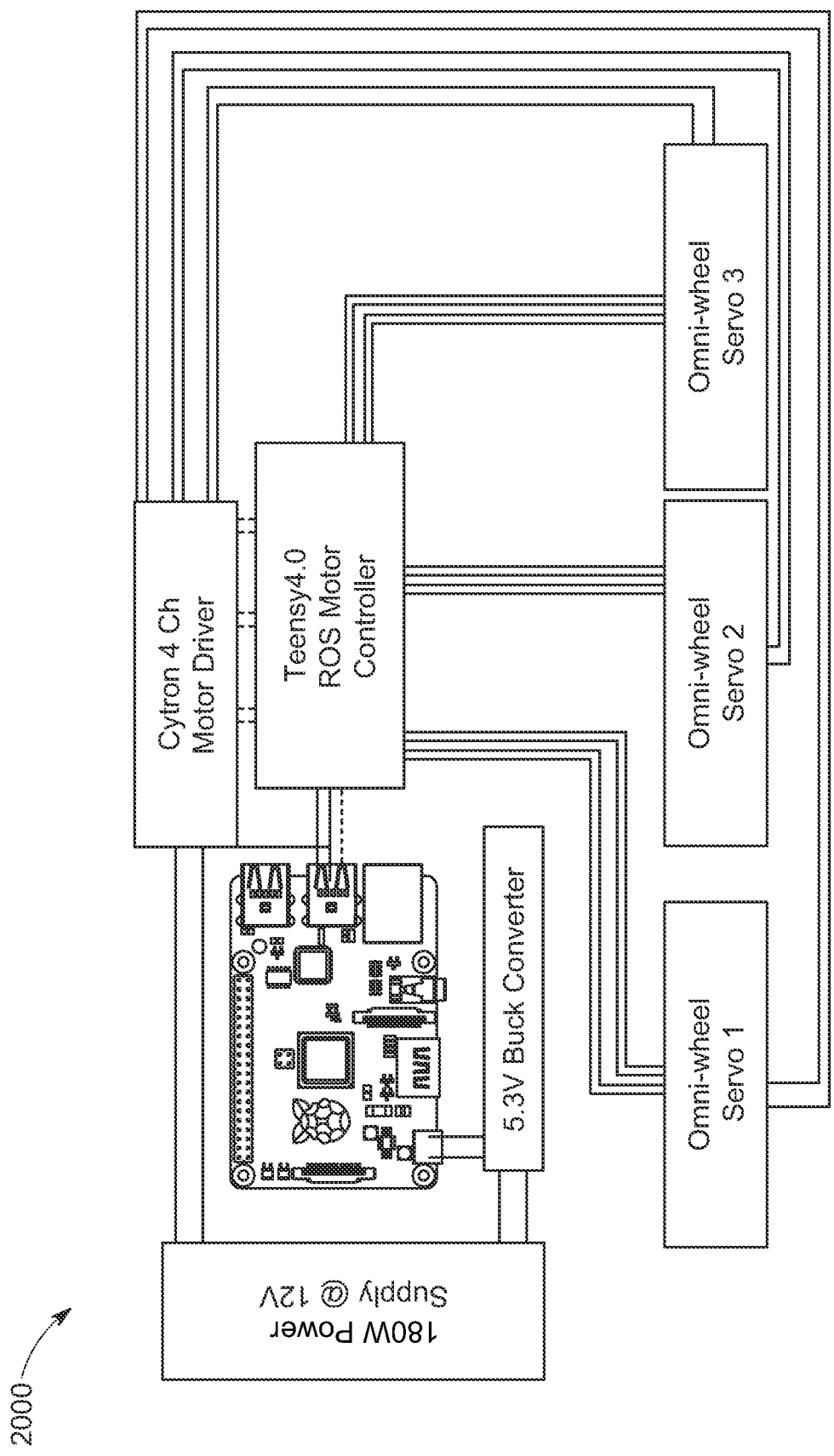
FIG. 20 is an omni-wheel base wiring diagram of components of the therapeutic social robot according to an embodiment of the disclosure.

FIG. 20 shows an omni-wheel base wiring diagram 2000. Again, a RPi is used as the central computer, which allows for wireless communication over ROS protocol so that commands can be sent from the main RPi controller in the Torso. Over USB, the RPi powers the Teensy4.0 Motor controller (a commercially available component) and sends command signals through ROS Serial protocol. From here the RPi is not connected to any other systems and the Teensy4.0 interfaces with the Cytron FD04A (a commercially available component) motor driver. This is done via 20 KHz PWM to control speed and direction is done via standard 10 pin. Using 20 KHz ultrasonic PWM allows for silent motor operation, although it is slightly out of spec for the motor driver. The PWM and direction pin are represented by the dashed lines connecting the Teensy 4.0 and the Cytron. It should also be noted that the Teensy4.0 and the Motor Driver share a common ground so that the PWM and Dir signals share a reference. The output of the motor driver is then the power to the motors, which can be seen exiting the Cytron block in standard red and black DC power lines which connect to the Omni-wheel servos. The shaft mounted encoders may then be connected back to the Teensy4.0 for closed loop control. Here the blue and green lines represent 3.3V and ground to the encoder, while the white and yellow lines are the encoders A and B channels. Using this circuit, the Omni-wheel Base is completed; accepting commands from the main RPi in the torso, sending them to the Teensy4.0 which does PID control for motor position, creating the Omni-wheel Servos.

Computer Configuration and Code:

Now that the physical components of Nyku have been outlined and described, the computer architecture and the code to control Nyku is considered. First, the computer configuration that allows for the control will be explained. Second the control interfaces will be outlined and the flow charts presented for the control of the torso and neck. There is more code that runs Nyku, such as the Eye GUI, however this code is of the type known to those of skill in the art. To code Nyku with the most modern robotics standards, the computer systems may be configured to accept ROS and OpenCV 4. To allow for optimization of neural network tasks and provide a platform for future development hardware acceleration may be made compatible with the system. In Nyku, the Intel Movidious Neural Compute Stick (a commercially available component) is used for hardware acceleration of neural network tasks.

In the Nyku System, there are two main computers. One controls the torso, and the other controls the Omni-wheel base. In the Torso there is a Raspberry Pi 4B+ running a custom version of Raspbian Buster. The following paragraphs of the disclosure discuss exemplary test code used and run in experiments to validate the functionality of the code for the social robot.

Neck Control:

As the neck is built using Dynamixel servos, the control interface on the receiving side is already written. What is necessary is then to send the correct communications to the existing platform. To do this, the Dynamixel control hardware package is used to configure the hardware interface. Here a URDF file is used to name each servo, establish travel limits, define velocity limits, as well as establish link connections, which may be stored in a URDF folder in the package. A YAML file doing the same is also required, but it is stored in the Neck control package ("neck dyna test"). In the neck dyna test, the control for the neck is done using all three methods exposed by the Dynamixel control hardware package. Included in the neck dyna test package there are examples covering control of the neck via an action client, a service client, and a direct communication with the command interface of the action client. The purpose of this package was to test which method of communication created the smoothest motion in the neck. It was found that interfacing with the action as a client provided the smoothest motion.

Omni-Wheel Base Control

In order to control the base, an interface for sending goal positions to the omni-wheel servos had to be determined. Unlike the Dynamixel neck, this interface was written from scratch. To tackle this problem, first a PID controller had to be implemented on the Teensy4.0 which so that the position of the omni-wheel servos could reliably be specified. This is done using a standard PID algorithm, where the error between the desired and actual position is taken into account with the integral and the derivative of the error, each modified by their respective gains. In the PID controller, anti-windup for the integral term was implemented in order to keep the system stable during long periods of operation. A significant dead band tolerance was also implemented as the shaft encoders were more precise that allowed by the backlash in the gear train of the motors.

Initially, this PID controller was tested by manually sending goal positions via a serial monitor. As the Teensy4.0 can be coded in C++ with Arduino libraries, the serial communication protocol of Arduino was used to write a parser which could decompose a string of goal positions into an array of integers needed in the PID algorithm.

However this method proved to have some issues. Although difficult at first, it was possible to send the correct string of goal positions from C++ using the termios library. This worked for initial testing, but when using the motor controller as an output to a main control pipeline, the motor controller on the Teensy4.0 had to report its status. When attempting to use the termios library to read from the port, timing the communication was extremely hard. The main pipeline would read the string of correct length, however it could not be synced to the start and end of the string being sent from the Teensy over serial. Without feedback from the motor position, the motion of the servos was discontinuous due to an arbitrary wait times included in order to ensure completion of a goal.

When researching to solve this issue, it was discovered that some microcontrollers could be coded to accept a rosserial interface. Although the Teensy4.0 was not part of the included controllers, very small changes to the rosserial arduino package allowed the use the Teensy4.0 as ROS node, making it as robust as any other ROS enabled peripheral. With this the use of ROS topics on the microcontroller was possible. Thus, the input and output pipeline of the motor controller on the Teensy4.0 was edited to receive an array of goal positions for the servos and return their error via an array of the same type. With this completed, control of the omni-wheel servos was finally reliable.

This source code can be found in the Teensy4MotorController repository in the ros-control branch. In order to run initialize the node, one may create a custom launch file specifying the serial port that the rosserial interface is looking for as well as the baud rate. Once the rosserial node is started it will automatically forward the topics to and from the Teensy4.0 motor controller.

Now that individual positions could be sent to the Teensy4MotorController, it was necessary to find what omni-wheel servo positions would result in the desired hemisphere orientation. This is discussed at length later in this disclosure, in the section where inverse kinematics are derived. For the purposes of the present description, it suffices to say that the joint angle calculations were implemented in a C++ library called eq man ik. Using this, the goal orientation of the hemisphere can be specified in RPY angles. To validate this a few test pipelines were established, and can be found in the nyku omniwheel base repository.

Figure 21:
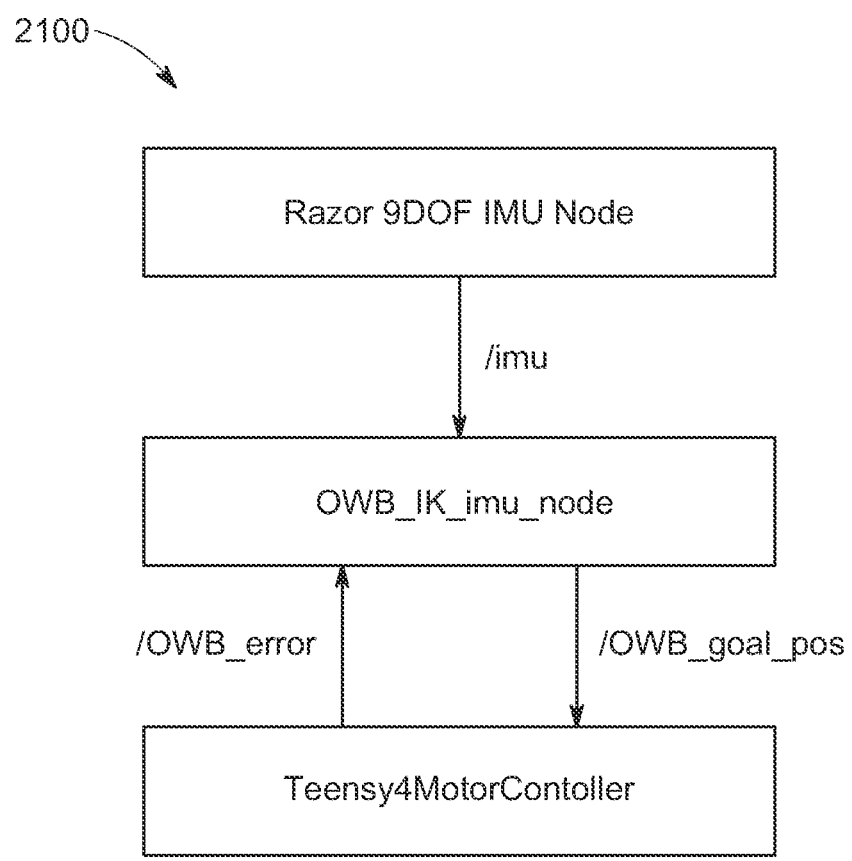
FIG. 21 is a node diagram for an IMU control pipeline that may be used in embodiments of the therapeutic social robot.

First, a Razor 9DOF IMU was used as an input to the pipeline to create the goal positions, which were then sent to the motor controller on the Teensy4.0. The node diagram 2100 for this pipeline can be seen in FIG. 21.

Figure 22:
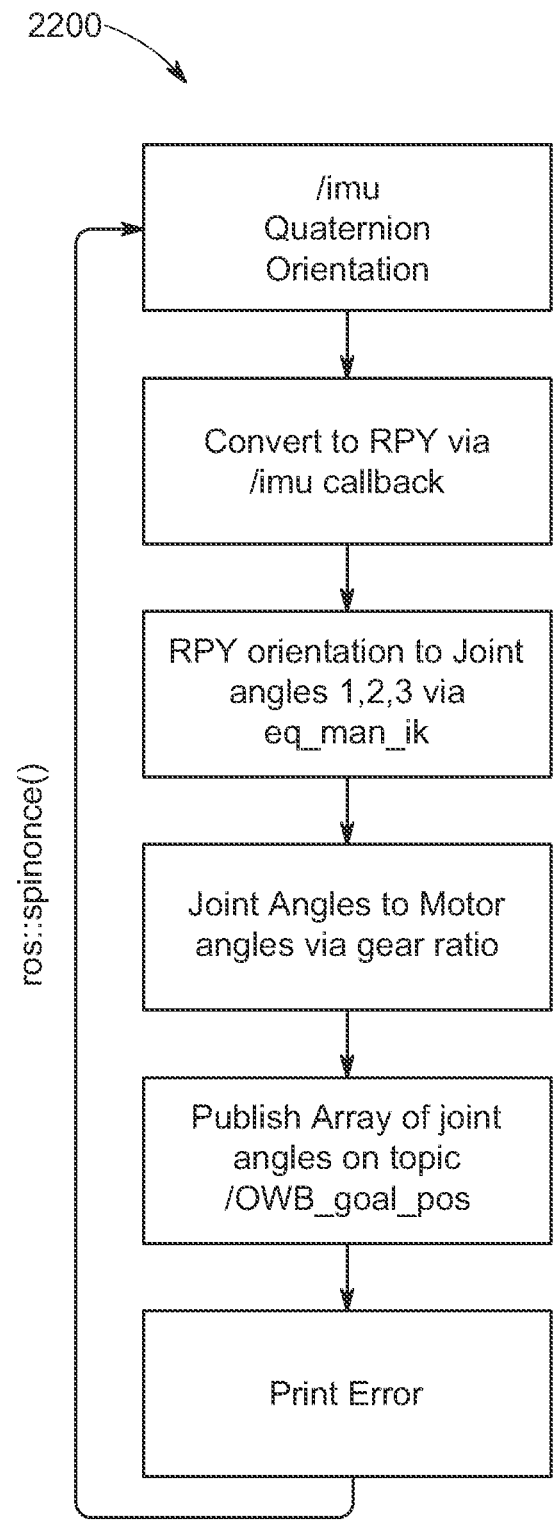
FIG. 22 is a pipeline flow chart for IMU control that may be used in embodiments of the therapeutic social robot.

Here the OWB IK imu node subscribes to the quaternion orientation from the/imu topic. This is the converted to RPY orientation in the callback for the razor IMU subscriber. This RPY orientation is then fed into the inverse kinematics calculator and the resulting joint angles are converted through the gear ratio of the omni-wheel to hemisphere interface, and then sent to the Teensy4MotorController which reports back the error. This flow 2200 is illustrated in FIG. 22. While ROS is "OK" this loop continues and the hemisphere mimics the orientation of the IMU.

Figure 23:
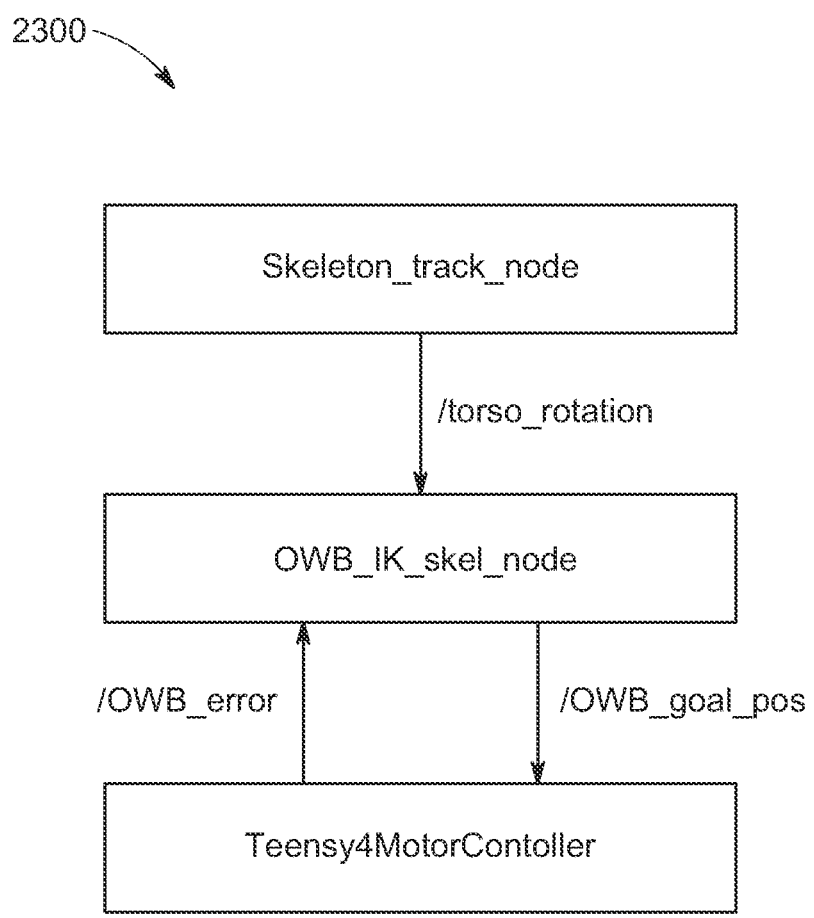
FIG. 23 is a node diagram for skeleton tracking in a control pipeline that may be used in embodiments of the therapeutic social robot.
Figure 24:
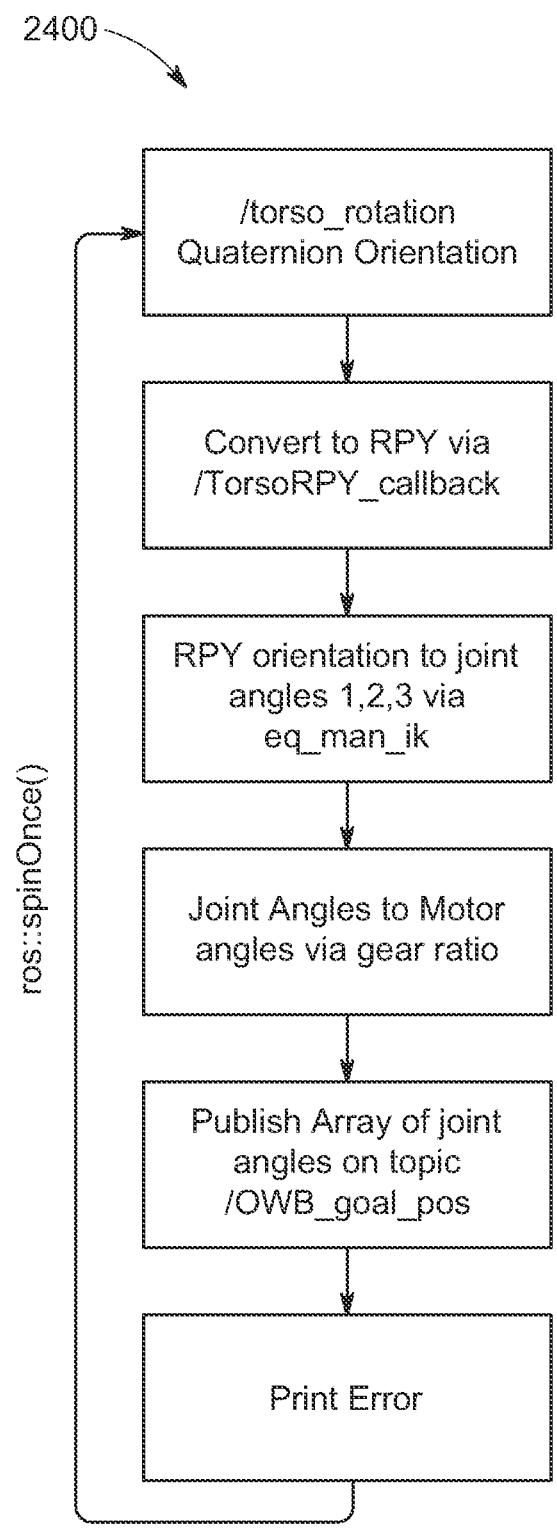
FIG. 24 is a pipeline flow chart for skeleton tracking control that may be used in embodiments of the therapeutic social robot.

Similarly to the IMU controlled pipeline, the Skeleton tracking control pipeline 2300 takes quaternion orientation of the torso as seen in the node diagram shown in FIG. 23. Here, the OWB IK skel node subscribes to the/torso rotation topic and converts it into the necessary joint angles. Here however there is not a prebuilt ROS node for skeleton tracking. Skeleton tracking is implemented using the Nuitrack SDK and an Intel RealSense D435 RGBD Camera following their documentation. In/skeleton track node, the torso orientation is isolated and published to the/torso rotation topic feeding into the pipeline 2400 in FIG. 24.

Although the pipelines for the IMU and skeleton tracking control look similar, there is a slight difference in the quaternion conversions. The/imu topic uses a sensor msgs::Imu message as opposed to the/torso rotation topic which publishes a geometry msgs::Pose.

These were the preliminary tests run using the IK model described later in the disclosure. They were conducted in order to validate the control pipelines visually. Using the IMU to control the orientation of the sphere was very effective as there was a 1:1 mapping of orientation and it was intuitive. However, when the skeleton tracking was used to control the orientation of the hemisphere, the orientation of the Torso was difficult to map to the sphere. As the coordinate systems are not aligned, rotations about the axes were not mapped directly. This is to say that torso yaw resulted in Omni-wheel Base pitch and so forth. This problem was exacerbated by the lack of Nuitrack documentation describing the home orientation of the joints. Due to the three minute limit on the Nuitrack software and the difficulty recording a motion for playback this mapping was hard to determine experimentally.

Figure 25:
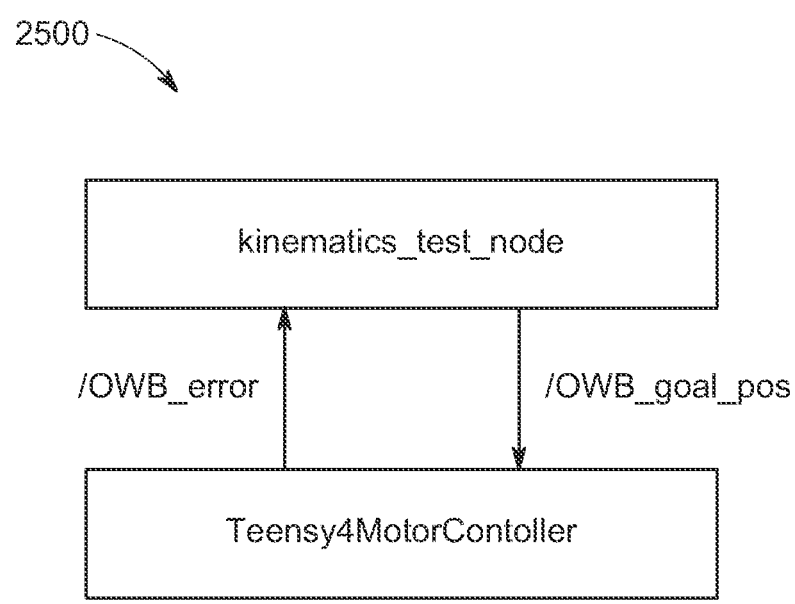
FIG. 25 is a node diagram for an 1K testing pipeline that may be used in embodiments of the therapeutic social robot.
Figure 26:
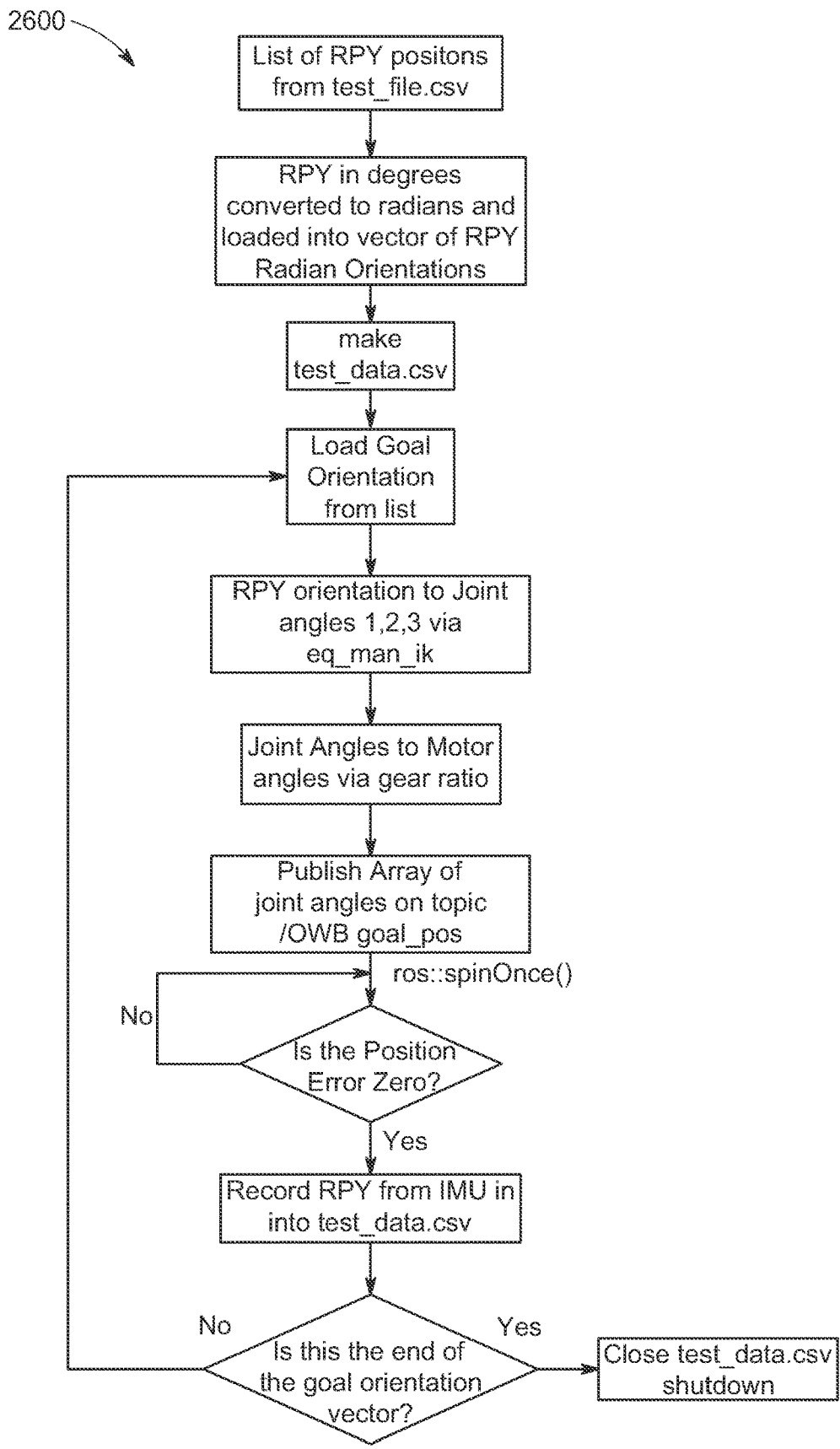
FIG. 26 is a pipeline flow chart for 1K testing.

The first step in solving the above issue was to write a program to test the performance of the systems developed in this thesis and then try to solve compatibility issues with the Nuitrack software. As such, a test plan was developed using the following pipeline 2500, as in FIG. 25. The test procedure itself is fully described later in this disclosure, but it is also shown in FIG. 26 in the test procedure flowchart 2600.

In short, a CSV file of desired orientations is read into a vector of float vectors in C++ representing the desired RPY for a certain trajectory point. This goal orientation vector is then run through in order and its IK calculated, applied to the motors, and the resulting RPY is measured with the IMU. This IMU recorded data is then stored in a data CSV created each time the test program is run with a time stamped name for clarity.

Omni-Wheel Kinematics:

Experiments and background of Omni-Wheel Base Control. In prior art designs of ball-balancing robots, the robot sits on top of a ball through an Omni-wheel interface which is an inverted version of Nyku's Omni-Wheel base discussed in the previous chapter. In these types of robots the controllable parameters of these systems are the angular velocities of the omni-wheels, not the positions of the omni-wheels. This is because the sphere is used for locomotion and the control is not concerned with the orientation of the ball itself. In prior art control schemes, they are concerned with the orientation of the robot above the ball and the robots position in the navigable environment. Some have developed the kinematics of the model using a Lagrangian method and achieve control using a Linear Quadratic Controller outputting wheel velocities. Others have built their own ball balancing robot on a similar LQR method, but again, each of these prior art control schemes concern the position of the robot in the navigation plane, not the orientation of the sphere.

Another prior art design, the Atlas sphere is closer to the approach of the present disclosure. In the prior art approach, the ball sits on top of the omni-wheels This system developed by researchers at Carleton University was designed to be a 6 DOF simulator for testing equipment as well as training pilots. Their system mounts the sphere on an XYZ linear motion table as well, allowing for motion in all 3 Cartesian directions as well as rotations about all axes. Given the infinite rotation possible on the sphere, it is possible to simulate all forces that would act on the ball. The Atlas sphere control scheme uses a mapping of tangential velocity from omni-wheel to sphere. This team has also extended their work to acceleration level kinematics, through simple derivation. However, when they tried to integrate the velocity level kinematics to position, the team was only able to achieve an estimate by numerically integrating quaternion rotations. This will be explored briefly in the next section as it is more applicable to the architecture of Nyku's Omni-wheel base and inform the design of the presently disclosed kinematic model.

In the development of the Omni-wheel sphere for Nyku, the design goal of posture mimicry dictates that position level control is better suited. And due to the computational restrictions of embedded micro-controllers such as the Raspberry Pi, an analytic solution is highly preferred. As such a kinematic equation was developed so that joint angles could be analytically solved given a goal orientation. The present disclosure provides novel analytical solution for the inverse kinematics of an omni-wheel/sphere mechanism's orientation.

Equivalent Manipulator Kinematics for Omni-Wheel Base

Figure 27:
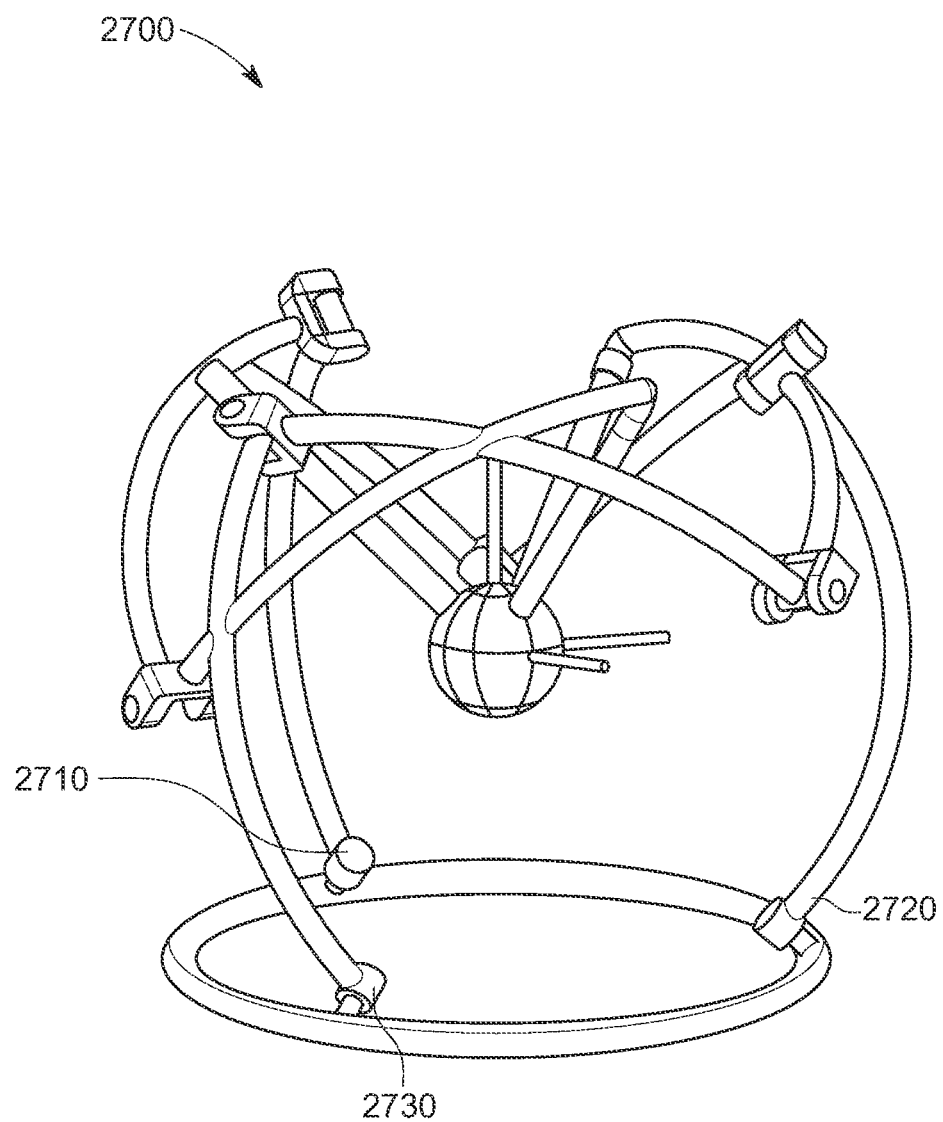
FIG. 27 is a model showing actions of three manipulators on a final frame for modeling kinematics of aspects of the social robot of the present disclosure.

In this section the kinematics for the equivalent manipulator model of the Omni-wheel Base are discussed. This system is modeled as a parallel mechanism consisting of three serial link 3 DOF manipulators with intersecting axes, as seen in FIG. 27. In this figure, we see all three manipulators contributing to the orientation of the last frame, represented by the checkered ball. Here, each manipulator is labeled; A (2710), B (2720), and C (2730). Each manipulator comprises three serial links, connected to a common base and common end effector. As seen in this figure, the arms from different manipulators are intersecting. This illustrates the impracticality of actually building this system, and that it can only be used as a model for the system.

These manipulators are aligned according to the position of the motors in the base, 120 degrees apart at an elevation angle of 45 degrees, which are fixed angles defined by the structure of the base. From this orientation, the 3 DOF equivalent manipulator begins with its intersecting axes. The rotations caused by the manipulator are then projected back through the transformations of the motor structure and as such the rotations are referenced back to the home frame allowing for goal orientation to be defined in the intuitive inertial base frame. By modeling the Omni-wheel Base as a parallel mechanism of three serial link manipulators, each with 3 intersecting DOF, we are able to draw two conclusions. 1a) That each manipulator of the parallel mechanism contributes to the same goal, and 2) that because there are three consecutive intersecting axes, an analytic solution exists.

Armed with this information, we will now begin a discussion as to how the analytic solution of the 3 DOF intersecting axes manipulator is used to find the joint angles of the omni-wheel motors.

Equation 4.1 gives the forward kinematics for an individual manipulator in the home frame. As all of the axes of rotation intersect, as illustrated in the diagram 2800 of FIG. 28, all rotations can be expressed as 3×3 matrices, omitting the linear translations present in 4×4 rotation matrices. As such, $R^{06}$ is a 3×3 generic rotation matrix for one motor mechanism contributing to the orientation of the hemisphere. The forward kinematics are assembled from the base to the end effector using the moving frame Euler X-Y-Z convention. Naming convention is as follows; $R_z^{01}$ is the rotation from frame 0 to 1 about the Z axis.

Equation 4.1:

$$R^{06}=(R_x^{01}R_y^{12})(R_x^{23}R_y^{34}R_z^{45})((R_y^{12})^T(R_z^{01})^T) \quad (4.1)$$

Where the individual contributing rotations are of standard forms as shown in Equation 4.2 with $s\theta=\sin(\theta)$ and $c\theta=\cos(\theta)$ of some arbitrary rotation angle $\theta$.

Equation 4.2

$$R_x=\begin{bmatrix}1 & 0 & 0\\0 & c\theta & -s\theta\\0 & s\theta & c\theta\end{bmatrix} R_y=\begin{bmatrix}c\theta & 0 & s\theta\\0 & 1 & 0\\-s\theta & 0 & c\theta\end{bmatrix} R_z=\begin{bmatrix}c\theta & -s\theta & 0\\s\theta & c\theta & 0\\0 & 0 & 1\end{bmatrix} \quad (4.2)$$

Figure 28:
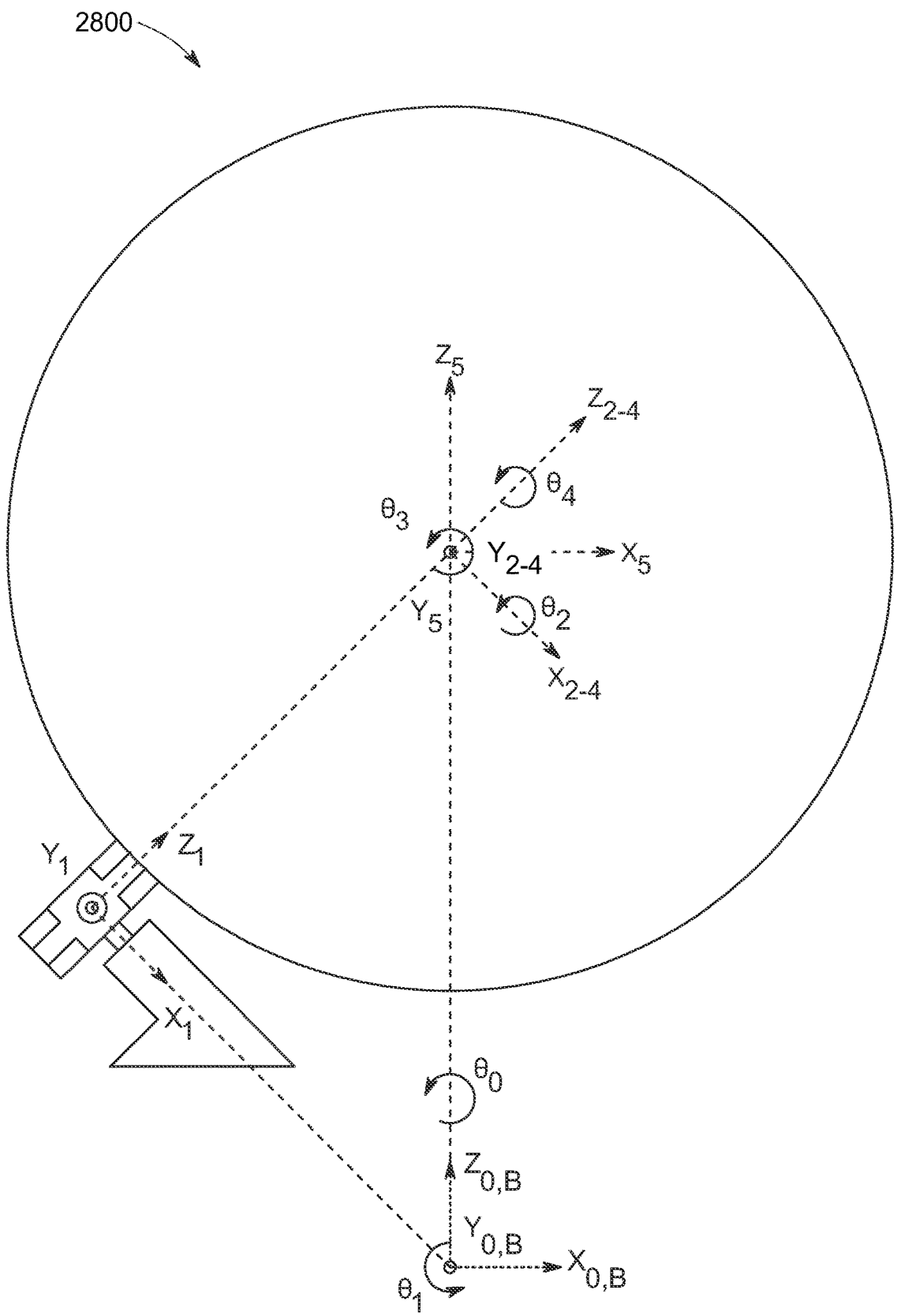
FIG. 28 is a diagram of reference frames for rotation of one equivalent manipulator depicted in FIG. 27.

In Equation 4.1, the terms are split by parentheses into groups. In the first group $(R_z^{01}R_y^{12})$, we have the rotations concerning the orientation of the motor, where $\theta_0$ is the rotation around the base Z axis corresponding to the 120 degree circular placement of the motor and $\theta_1$ is 45 degree elevation angle of the motor. In the second group, $(R_x^{23}R_y^{34}R_z^{45})$, we have the rotations that represent the degrees of freedom the omni-wheel. Here, $\theta_2$ is the motor's rotation angle about $X_2$. Although it appears that there is a linear displacement between $X_1$ and $X_2$ in FIG. 28, these axes are actually coincident and the mapping between them manifests mathematically as the gear ratio between the diameter of the ball and the diameter of the omni-wheel. $\theta_3$ is the pitch allowed across the omni-wheel rollers about $Y_3$, and $\theta_4$ is the less intuitive yaw about $Z_4$ which represents the twist that can occur at the tangent point between the sphere and the omni wheel. All three of these rotations are made possible by the omni-wheel, however only $\theta_2$ is controllable, while $\theta_3$ & $\theta_4$ are resultant based on the desired final orientation. In FIG. 28, reference frames 2 through 4 are shown as a combined frame with axes $X_{2\text{-}4}$, $Y_{2\text{-}4}$ & $Z_{2\text{-}4}$. The last group, $((R_y^{12})^T(R_z^{01})^T)$ is inverse rotation in order to return the final frame back into base coordinates so that it may be compared with the other 2 manipulators allowing for the specification of only one goal position in the control system. These rotations are clearly illustrated in FIG. 28.

Figure 29:
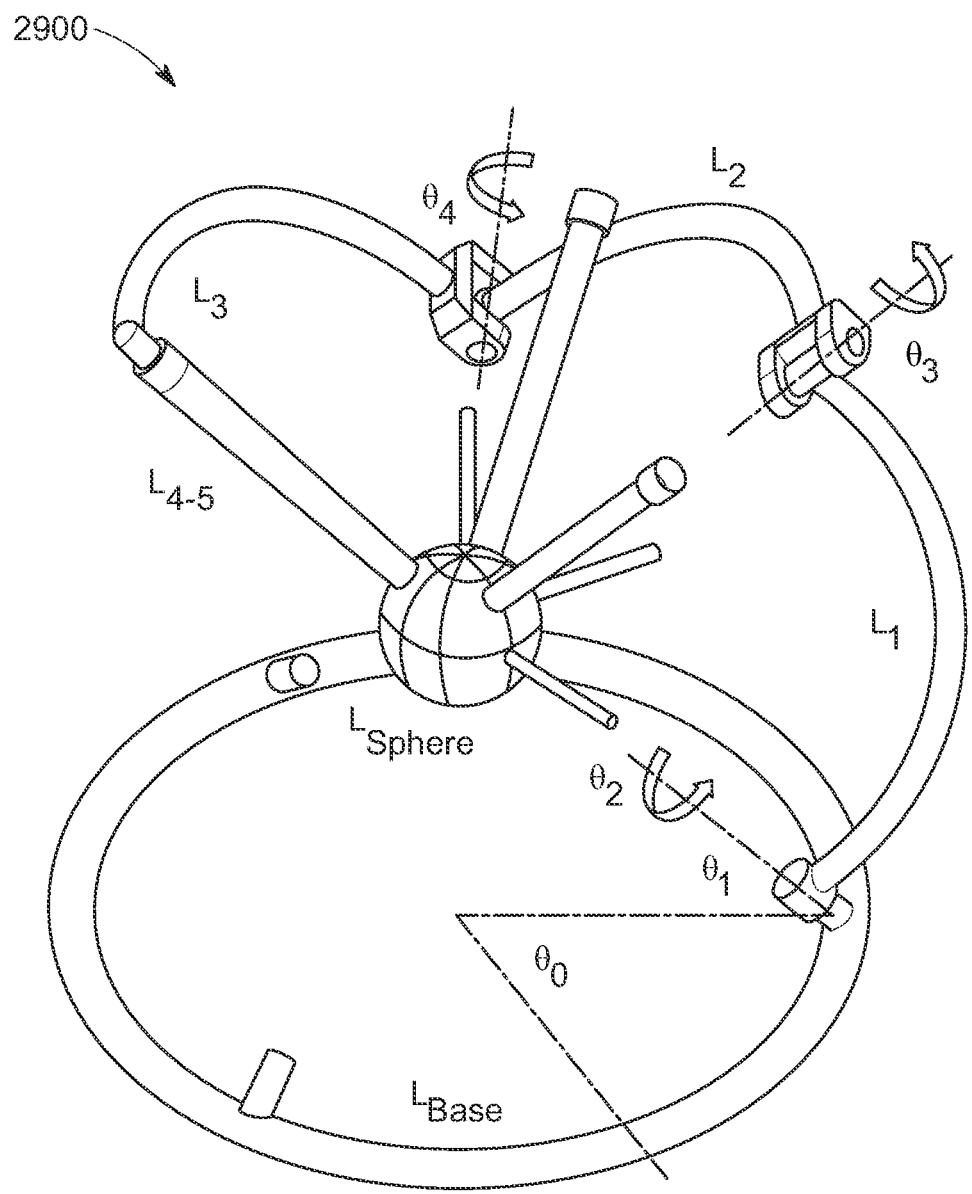
FIG. 29 is a model showing actions of one equivalent manipulator arm contributing to a goal orientation of the social robot of the present disclosure.

Another way to visualize the mechanism is to draw links between the axis and create such an arm as in the diagram 2900 of FIG. 29. Where the base represents the rotations that place the motors in their initial configurations, group $(R_z^{01}R_y^{12})$. The differently shaded arms represent the links in between $\theta_2$, $\theta_3$ & $\theta_4$, and form the mechanism described by $(R_x^{23}R_y^{34}R_z^{45})$. The checkered sphere in the middle represents the center of the fifth reference frame, while the triad extending from it represent the return rotations to this common frame, $((R_y^{12})^T(R_z^{01})^T)$. These extensions from the sphere are then clearly spaced out by 120 degrees around local Z and at 45 degrees about Y from vertical in their respective planes.

For clarity, the manipulators are discussed individually, however, the complete mechanism looks as it does in FIG. 27. So far, the forward kinematics of the mechanism have been established which give the final position of frame 5 if the joint angles, $\theta_2$, $\theta_3$ & $\theta_4$, are known. For Nyku's control purposes, we know the final goal which is our desired orientation of frame 5, the sphere, and the fixed angles of the mechanism. Now the forward kinematics are used to find an expression for the variable joint angles that result in our desired orientation. To do this, a goal rotation G is established, and set equal to the forward kinematics, $R^{06}$ Equation 4.3:

$$G=R_z(\theta_y)R_y(\theta_p)R_x(\theta_r) \quad (4.3)$$

Notice, that here G is defined in with fixed reference frame conventions such that the desired orientation of the final ball can be given more intuitively in standard roll $(\theta_r)$, pitch $(\theta_p)$, and yaw $(\theta_y)$ angles. As such, the rotations are taken in the order of Z-Y-X for pre-multiplication with the home frame. Notice that the subscript i is now added to the rotations indicating which arm, A, B, or C, the forward kinematics are computed for.

Equation 4.4:

$$G=R_i^{06}=(R_{zi}^{01}R_y^{12})(R_{xi}^{23}R_{yi}^{34}R_{zi}^{45})((R_y^{12})^T(R_{zi}^{01})^T) \quad ((4.4)$$

From here, the 3 DOF manipulator is isolated from the right hand side of the equation. For simplicity, we redefine the manipulator as $M_i$. Where, each rotation $R_i$ is a function of its joint angle $\theta_i$.

Equation 4.5:

$$M_i=R_{zi}^{23}(\theta_{2i})R_{yi}^{34}(\theta_{3i})R_{zi}^{45}(\theta_{4i}) \quad (4.5)$$

Here, the rotations on the right in Equation 4.5 are all with respect to the angles of the manipulator in question. This rotation is taken in the order X-Y-Z as we describe the manipulator from the base in the moving reference frame convention.

Equation 4.6:

$$G=(R_{zi}^{01}R_y^{12})M_i((R_y^{12})^T(R_{zi}^{01})^T) \quad (4.6)$$

Equation 4.7:

$$M_i=((R_y^{12})^T(R_{zi}^{01})^T)G(R_{zi}^{01}R_y^{12}) \quad (4.7)$$

The manipulator identifying i is dropped on $R^{12}$ as this rotation is common to all manipulators as is the goal G. The identifying i is also dropped within the matrix elements for brevity as well, but it should be noted that these are the angles of the individual manipulator. Now, on the left we have $M_i$ which is a 3×3 rotation matrix of the standard form:

Equation 4.8

$$M_i = \begin{bmatrix} c_3c_4 & -c_3c_4 & s_3 \\ c_2s_3 + s_2s_3c_4 & c_2c_3 - s_2s_3s_4 & -s_2c_3 \\ s_2s_4 - c_2c_4s_3 & s_2c_3 + c_2s_3s_4 & c_2c_3 \end{bmatrix} \quad (4.8)$$

where $s_2 = \sin(\theta_1)$ and $c_4 = \cos(\theta_4)$ etc.

The right hand side of Equation 4.7 is entirely known and will therefore be a 3×3 numeric rotation matrix which we will denote as Gi, with elements labeled as in Equation 4.9.

Equation 4.9

$$G_i = \begin{bmatrix} r_{11} & r_{12} & r_{13} \\ r_{21} & r_{22} & r_{23} \\ r_{31} & r_{32} & r_{33} \end{bmatrix} \quad (4.9)$$

Substituting $M_i = G_i$ we have:

Equation 4.10

$$\begin{bmatrix} c_3c_4 & -c_3c_4 & s_3 \\ c_2s_3 + s_2s_3c_4 & c_2c_3 - s_2s_3s_4 & -s_2c_3 \\ s_2s_4 - c_2c_4s_3 & s_2c_3 + c_2s_3s_4 & c_2c_3 \end{bmatrix} = \begin{bmatrix} r_{11} & r_{12} & r_{13} \\ r_{21} & r_{22} & r_{23} \\ r_{31} & r_{32} & r_{33} \end{bmatrix} \quad (4.10)$$

For the purposes of this solution we will be focusing on only the elements shown in Equation 4.11.

Equation 4.11

$$\begin{bmatrix} c_3c_4 & -c_3c_4 & s_3 \\ \cdot\cdot & \cdot\cdot & -s_2c_3 \\ \cdot\cdot & \cdot\cdot & c_2c_3 \end{bmatrix} = \begin{bmatrix} r_{11} & r_{12} & r_{13} \\ \cdot\cdot & \cdot\cdot & r_{23} \\ \cdot\cdot & \cdot\cdot & r_{33} \end{bmatrix} \quad (4.11)$$

From Equation 4.11 we can make the following simplifications using trigonometric identities to find our joints angles, starting with $\theta_3$:

Equation 4.12

$$r_{23}^2 + r_{33}^2 = -(s_2c_3)^2 + (c_2c_3)^2 = c_3^2(s_2^2 + c_2^2) = c_3^2 \quad (4.12)$$

$$c_3 = \sqrt{r_{23}^2 + r_{33}^2}$$

$$r_{13} = s_3$$

$$\tan(\theta_3) = \frac{s_3}{c_3}$$

$$\theta_3 = a\text{Tan2}\left(\frac{r_{13}}{\sqrt{r_{23}^2 + r_{33}^2}}\right)$$

Where a Tan 2 is the four quadrant arc tangent that returns the result from 0 to $2\pi$. We now use this value in our calculations of $\theta_2$ and $\theta_4$.

$$\frac{-r_{23}}{r_{33}} = \frac{s_2c_3}{c_2c_3}$$

$$\tan(\theta_2) = \frac{-r_{23}}{r_{33}} = \frac{s_2}{c_2}$$

Although $c_3$ simplifies our here, we maintain its sign in order to preserve the functionality of a Tan 2 in Equation 4.13 below.

Equation 4.13

$$\theta_2 = a\text{Tan2}\left(\frac{-r_{23} \times \text{sign}[c_3]}{r_{33} \times \text{sign}[c_3]}\right) \quad (4.13)$$

Last, $\theta_4$ is calculated using a similar procedure to $\theta_2$.

Equation 4.14

$$\frac{-r_{12}}{r_{11}} = \frac{s_4c_3}{c_4c_3} \quad (4.14)$$

$$\tan(\theta_4) = \frac{-r_{12}}{r_{11}} = \frac{s_4}{c_4}$$

$$\theta_4 = a\text{Tan2}\left(\frac{-r_{12} \times \text{sign}[c_3]}{r_{11} \times \text{sign}[c_3]}\right)$$

In Equation 4.15, the procedure for calculation is organized for clarity and re annotated for individual manipulators.

Equation 4.15

$$\theta_{3i} = a\text{Tan2}\left(\frac{r_{13i}}{\sqrt{r_{23i}^2 + r_{33i}^2}}\right) \quad (4.15)$$

$$\theta_{2i} = a\text{Tan2}\left(\frac{-r_{23i} \times \text{sign}[c_3 i]}{r_{33i} \times \text{sign}[c_3 i]}\right)$$

$$\theta_{4i} = a\text{Tan2}\left(\frac{-r_{12i} \times \text{sign}[c_3 i]}{r_{11i} \times \text{sign}[c_3 i]}\right)$$

The procedure is then followed for each manipulator, A, B, and C such that the solution matrix in Equation 4.16 can be assembled. In this matrix the top row represents the controllable motor angles before applying the gear ratio from sphere to omni-wheel.

Equation 4.16

$$\text{Solution} = \begin{bmatrix} \theta_{2A} & \theta_{2B} & \theta_{2C} \\ \theta_{3A} & \theta_{3B} & \theta_{3C} \\ \theta_{4A} & \theta_{4B} & \theta_{4C} \end{bmatrix} \quad (4.16)$$

In order to verify that this solution is mathematically correct, the goal position is set to a specific orientation as defined by $\theta_r$, $\theta_p$ & $\theta_y$, and then the resulting joint angles are found for each equivalent manipulator. These joint angles are then used in the forward kinematic calculation resulting in the manipulator pose. the manipulator pose is then subtracted from the goal. If correct the difference matrix, D, should be all 0. This procedure is described mathematically below.

Equation 4.17:

$$D_i = G - R_i^{06}(\theta_{2i}, \theta_{3i}, \theta_{4i}) \quad (4.17)$$

Using Equation 4.17 as verification of the kinematics, the maximum element-wise difference was $-1.4 \times 10^{-17}$. As this number is practically 0, it is assumed that the kinematics are valid and that any error is caused by the calculation of trigonometric functions by the computer. The kinematics was also done using a fixed reference frame convention, the process to which is identical except the following changes:

Equation 4.18

$$R^{06}_{fixed} = \left((R^{12}_y)^T (R^{01}_z)^T\right)(R^{45}_z R^{34}_y R^{23}_x)(R^{01}_z R^{12}_y) \tag{4.18}$$

Equation 4.19

$$M_{i_{fixed}} = R^{45}_{zi}(\theta_{4i}) R^{34}_{yi}(\theta_{3i}) R^{23}_{xi}(\theta_{2i}) \tag{4.19}$$

Equation 4.20

$$\theta_{3i_{fixed}} = a\text{Tan}2\left(\frac{-r_{31i}}{\sqrt{r_{11i}^2 + r_{21i}^2}}\right) \tag{4.20}$$

$$\theta_{2i_{fixed}} = a\text{Tan}2\left(\frac{r_{32i} \times \text{sign}[c_3 i]}{r_{33i} \times \text{sign}[c_3 i]}\right)$$

$$\theta_{4i_{fixed}} = a\text{Tan}2\left(\frac{r_{21i} \times \text{sign}[c_3 i]}{r_{11i} \times \text{sign}[c_3 i]}\right)$$

When tested with Equation 4.17, the fixed frame equations also result in a zero matrix. However, these equations do not produce the same results as the equations for the moving reference frame, which had already been developed and tested when the fixed frame equations were tested. These equations require more analysis as their results give very similar results for motor angles. When compared to joint angles resulting from the moving frame calculations, $\theta_{2Cfixed}$ is numerically close to $\theta_{2Cmoving}$, however for $\theta_{2Bfixed}$ and $\theta_{2Bfixed}$, the fixed frame calculations are clearly twice the value of those done in moving frame. For joint angles on arm A, $\theta_{2Afixed}$ appears to be in the opposite quadrant of $\theta_{2Amoving}$.

Figure 30:
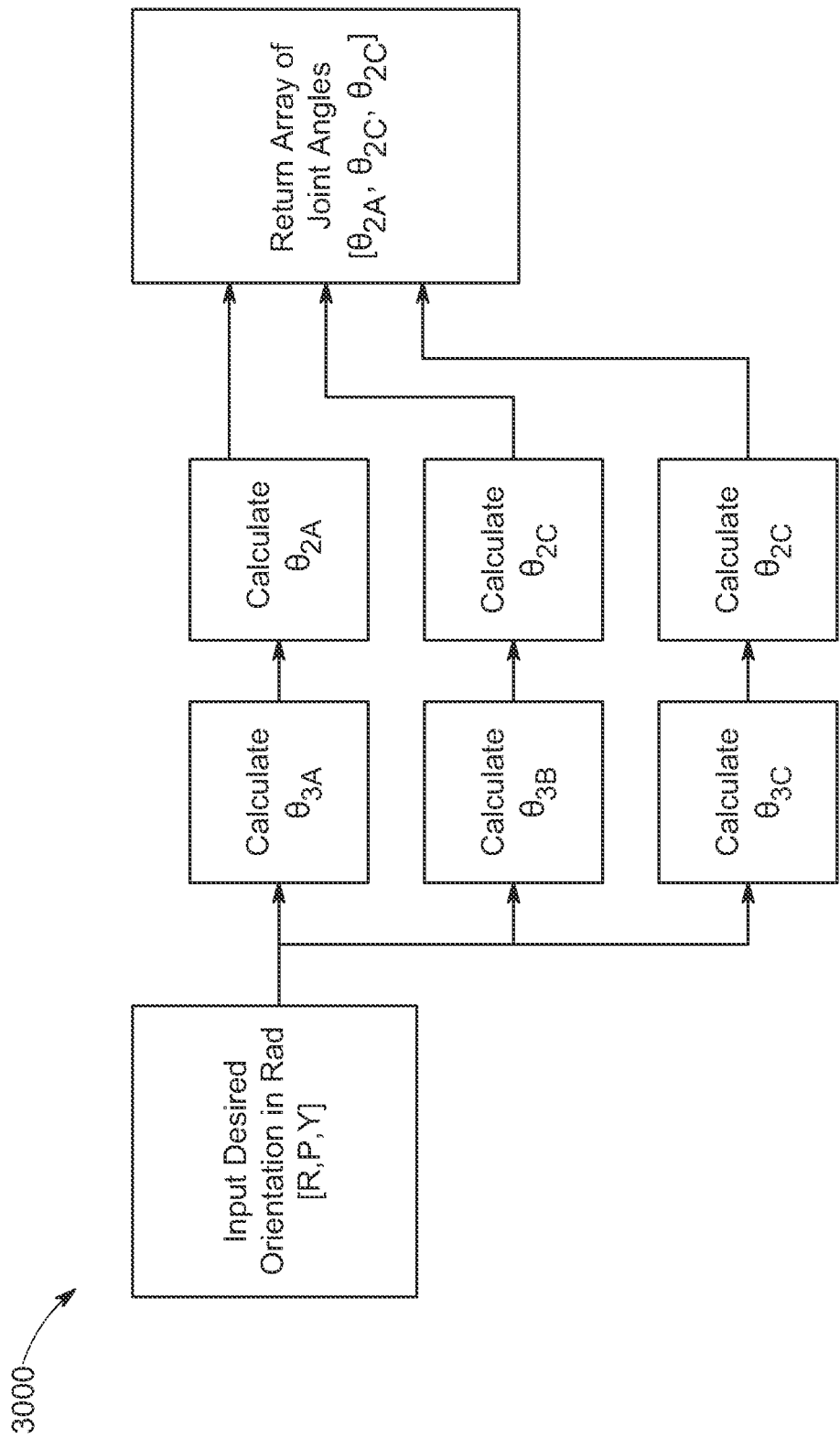
FIG. 30 is a flow chart for 1K calculation that may be used in embodiments of the therapeutic social robot.

Testing Procedure for Equivalent Manipulator Kinematics:

In order to validate the inverse kinematics developed in the previous section, the equations had to be tested on the mechanism itself. This was done by implementing the inverse kinematics in a C++ library, as illustrated in the flow chart 3000 FIG. 30. In this inverse kinematics library, the inputs are fed in as a vector of desired RPY angles in radians, where they are then used to form the terms given on the right hand side of calculations outlined in Equation 4.15. In practice, the analytical formula for each of the terms in these equations is found by symbolic substitution in Matlab, such that the terms in $G_i$ are represented by long trigonometric expressions dependent only on the input RPY angles. These expressions are not produced here for brevity. However, they be found in the GitHub repository provided in Appendix A. This is library is then used to create the test program in the ROS architecture as described in more detail previously in this disclosure. Additionally, this test was conducted with the ribs, hardware layers and neck removed from Nyku, leaving only the empty hemisphere on the Omni-wheel Base.

The test program takes a CSV file containing a list of desired orientations, and parses each row into a 3×1 goal orientation vector. This goal orientation vector is then fed through the inverse kinematics class and returns the three goal motor positions which are then sent to the PID controller on the ROS enabled Teensy4.0 motor controller. The test program then waits for the position error of the motors to be 0, and then waits for half a second, to guarantee stable IMU readings, before taking a quaternion reading, converting it, and recording the resultant RPY of the hemisphere in a CSV created when each test is run. A detailed flow chart 2600 for this program can be found in FIG. 26.

In order for this test to succeed, the IMU, in this case a Razor 9DOF IMU from Sparkfun, may be calibrated according to the manufacturers instructions. Next, the coordinate system of the IMU may be aligned with the coordinate system of the Omni-Wheel base. This is achieved by outputting the IMU orientation so that the orientation can be verified and then mounting the IMU in the correct position on the Hemisphere, which has a known coordinate system. Next the system is powered on and the test program is run with the corresponding CSV for the desired test. Once the test is complete the data is graphed with the goal RPY and the actual RPY of the mechanism on the same axis. Error between goal and actual orientation was calculated for each point with respect to Pi in order to avoid division issues when the goal position was 0. This data is also plotted as follows:

Equation 4.21

$$\text{error} = \left(\frac{goal_\theta - actual_\theta}{\pi}\right) * 100 \tag{4.21}$$

When graphing the data for yaw, the initial measured yaw is subtracted from all yaw data points and is labeled as the yaw offset on the graphs. This is done as the yaw measurements from the IMU experience large drift according to the manufacturer, meaning that the alignment initially done during mounting is not reliable. By subtracting the initial yaw, we are able to zero the IMU about that axis for each test.

Tests were developed for roll, pitch, and yaw motions individually as well as one combined test that sent a series of motions about all axes to the mechanism. The individual tests each had 199 goal orientations, and the combined test had 121 goal orientations. These tests were limited to oscillations between ±30° about any axis. This was the limit of motion of the hemisphere so that its equator would not dip below the chord height projected onto the sphere by the omni-wheels. Yaw could have been tested with larger angles however the data would not have been as comparable between the axes. The combined test is intended to show that each axis of the goal orientation is independently controlled. The individual axis tests are intended to measure the repeatability of the system and detect any steady state error that may occur.

Omni-Wheel Inverse Kinematics Testing

Figure 31:
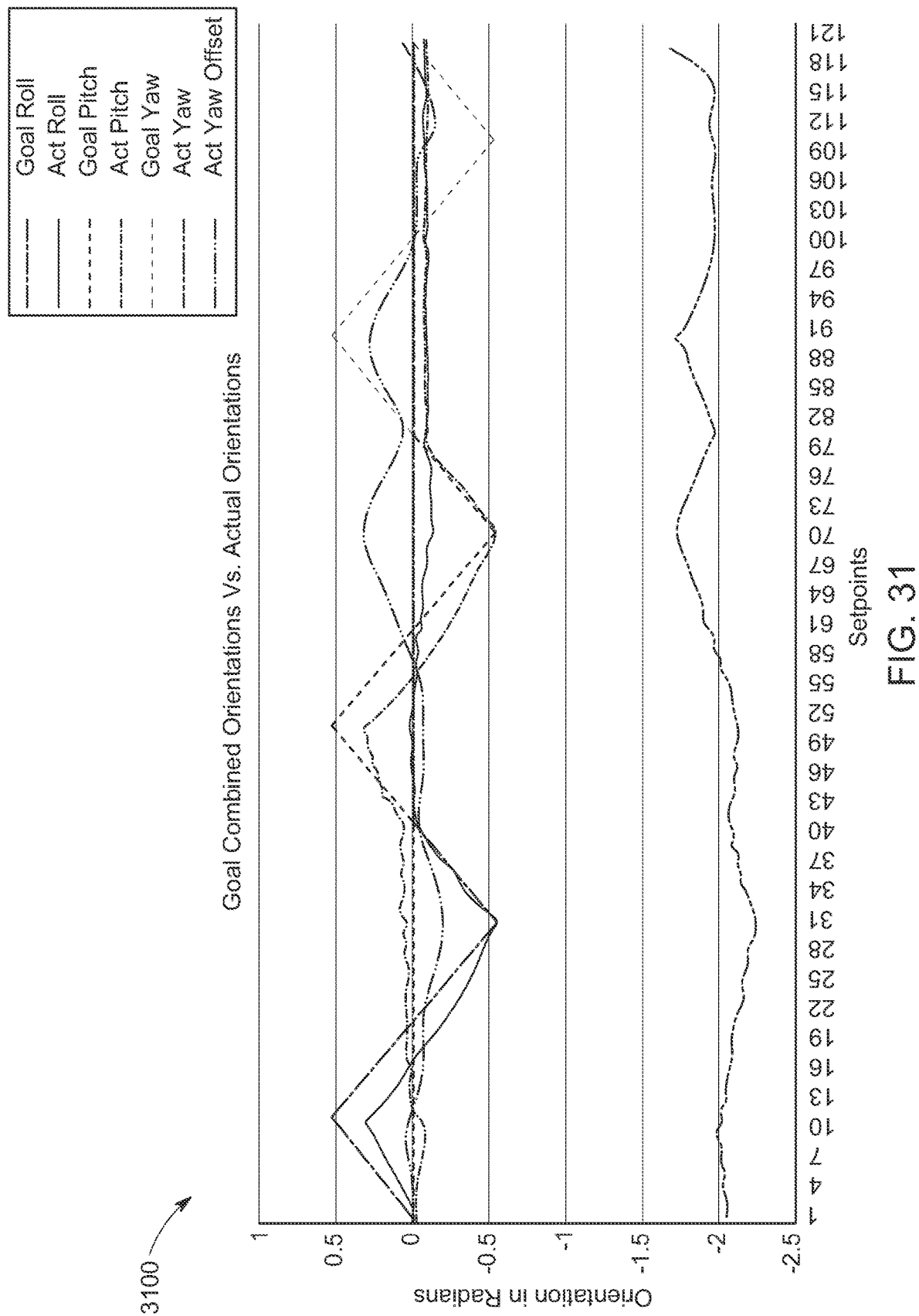
FIG. 31 is a graph showing combined orientation test results in experiments performed on embodiments of the therapeutic social robot.
Figure 32:
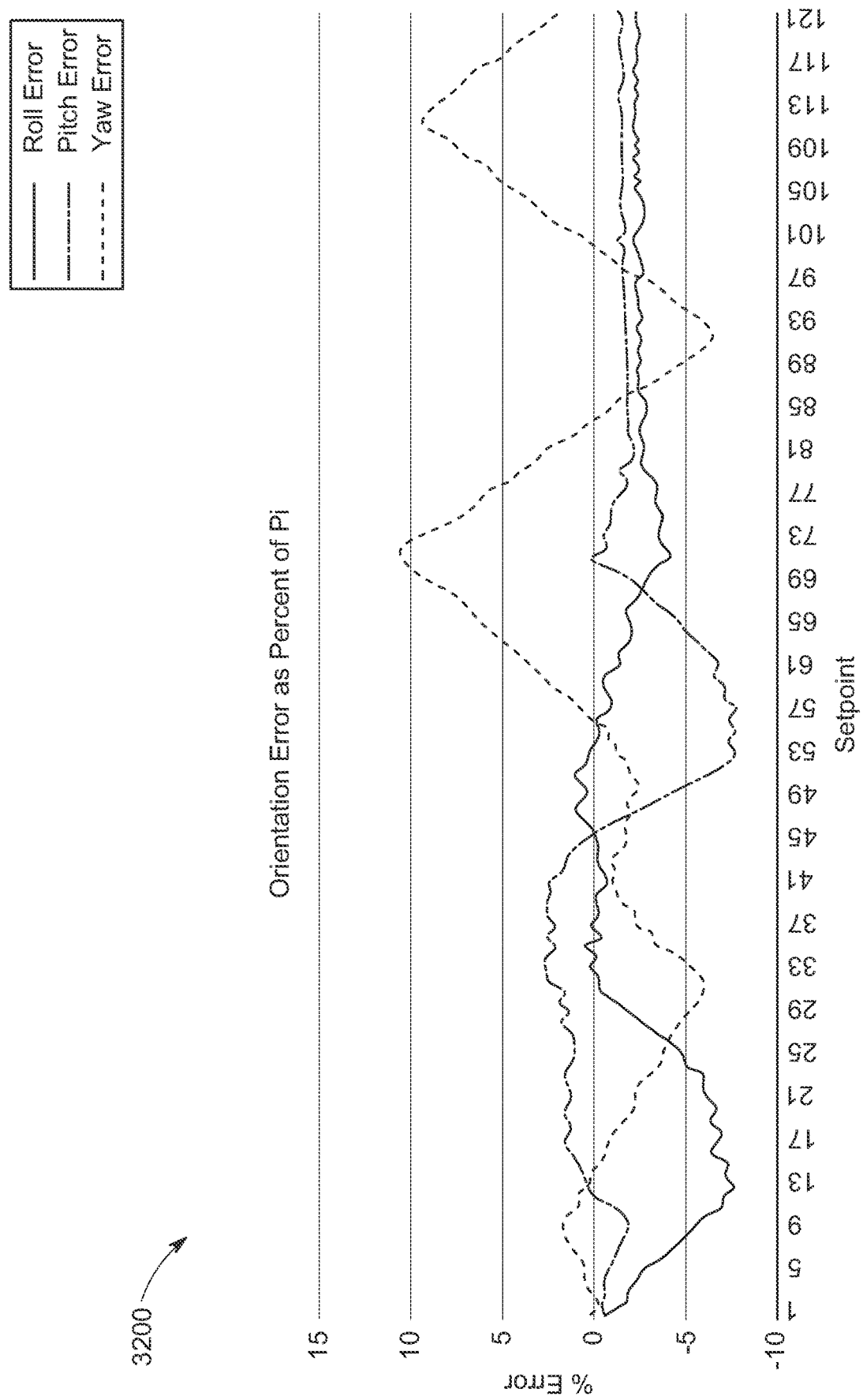
FIG. 32 is a graph showing combined orientation test error in experiments performed on embodiments of the therapeutic social robot.

The results of the testing described in the previous section are presented and discussed here. The graphs compiled from those tests are shown in subsequent figures. In FIG. 31 the test for combined motion is graphed in graph 3100. Here the Omni-wheel base oscillates the full range of motion about the x axis, follow by the y axis and finally the z axis. The actual position is found to trace the goal position well, except for note-able spikes in error for yaw when the negative pitch angle is set as the goal position. For roll and pitch angles, there is a maximum error of −8%, however, there is a spike of 11% in the yaw for the negative pitch angle, visible in graph 3200 FIG. 32. The next tests are focused on the repeatability of reaching target rotations about a singular axis.

Figure 33:
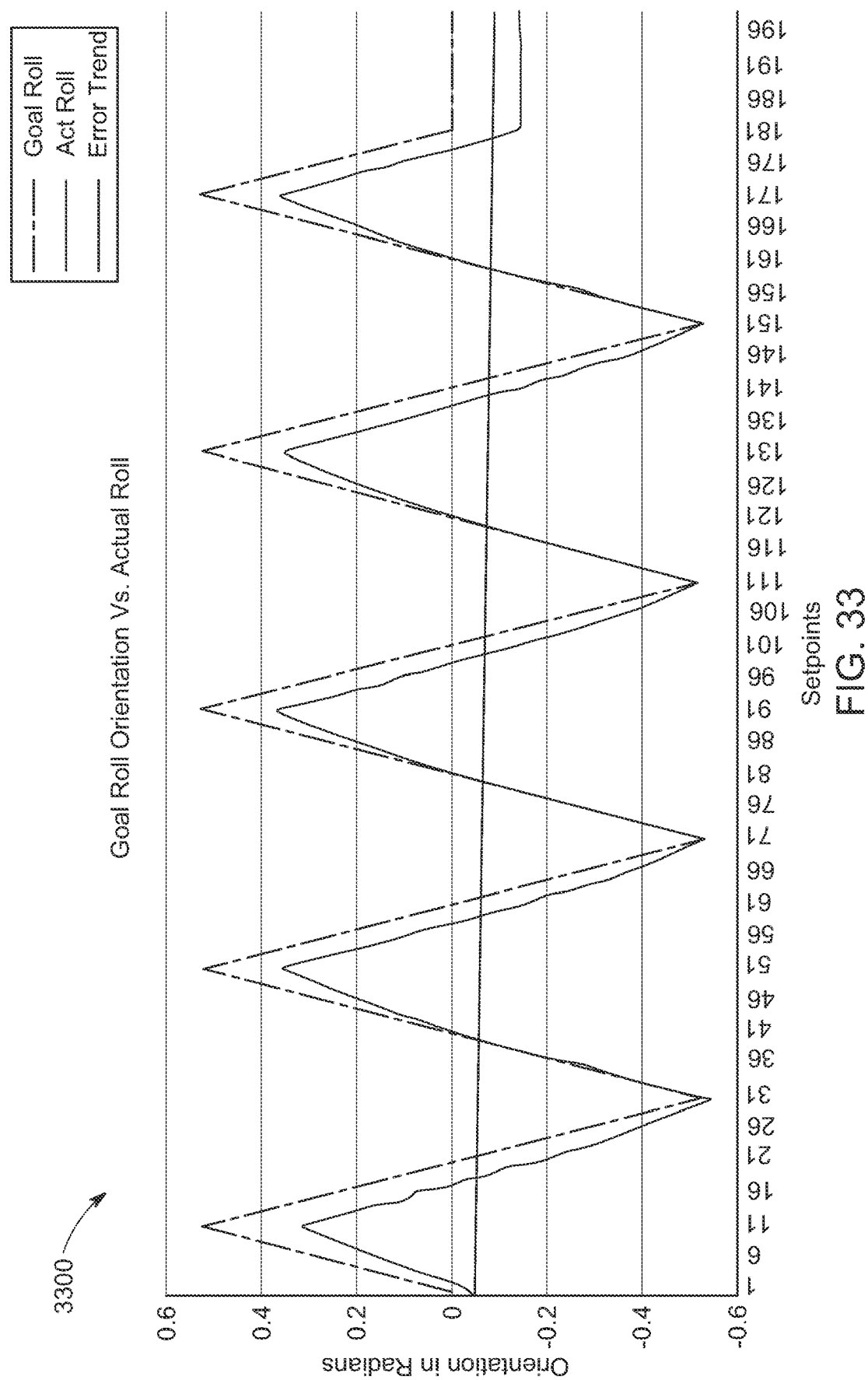
FIG. 33 is a graph showing roll orientation test results in experiments performed on embodiments of the therapeutic social robot.
Figure 34:
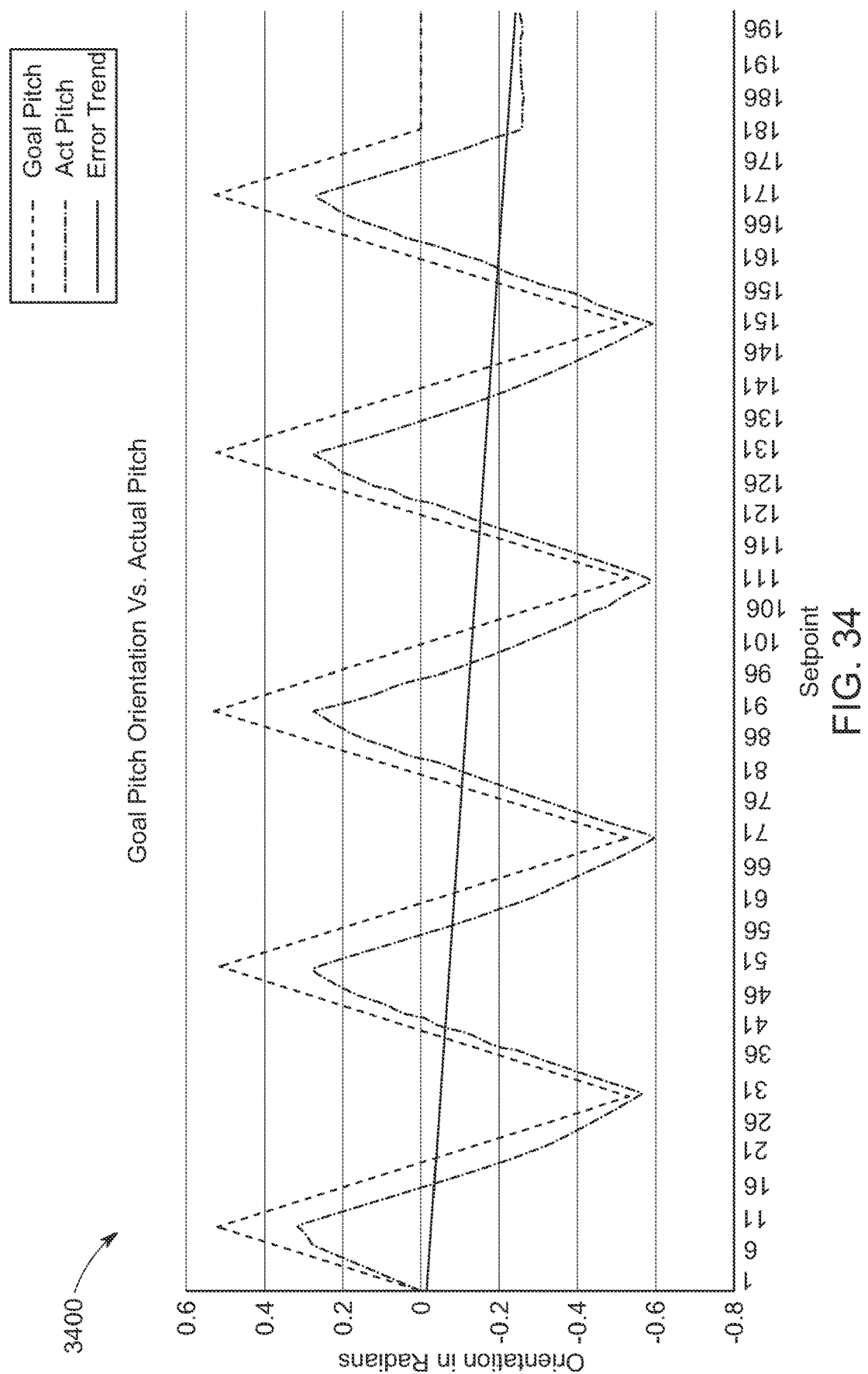
FIG. 34 is a graph showing pitch orientation test results in experiments performed on embodiments of the therapeutic social robot.

The repeatability tests are run in order; roll, pitch, yaw. Each test comprises four and a half oscillations in the range of motion and a stream of 20 goal orientations at 0 rotation where cumulative error can be examined. When looking at the pitch and roll tests in FIG. 34 (graph 3400) and FIG. 33 (graph 3300), it can be seen that the mechanism only reaches the goal position for negative goal rotations.

Figure 35:
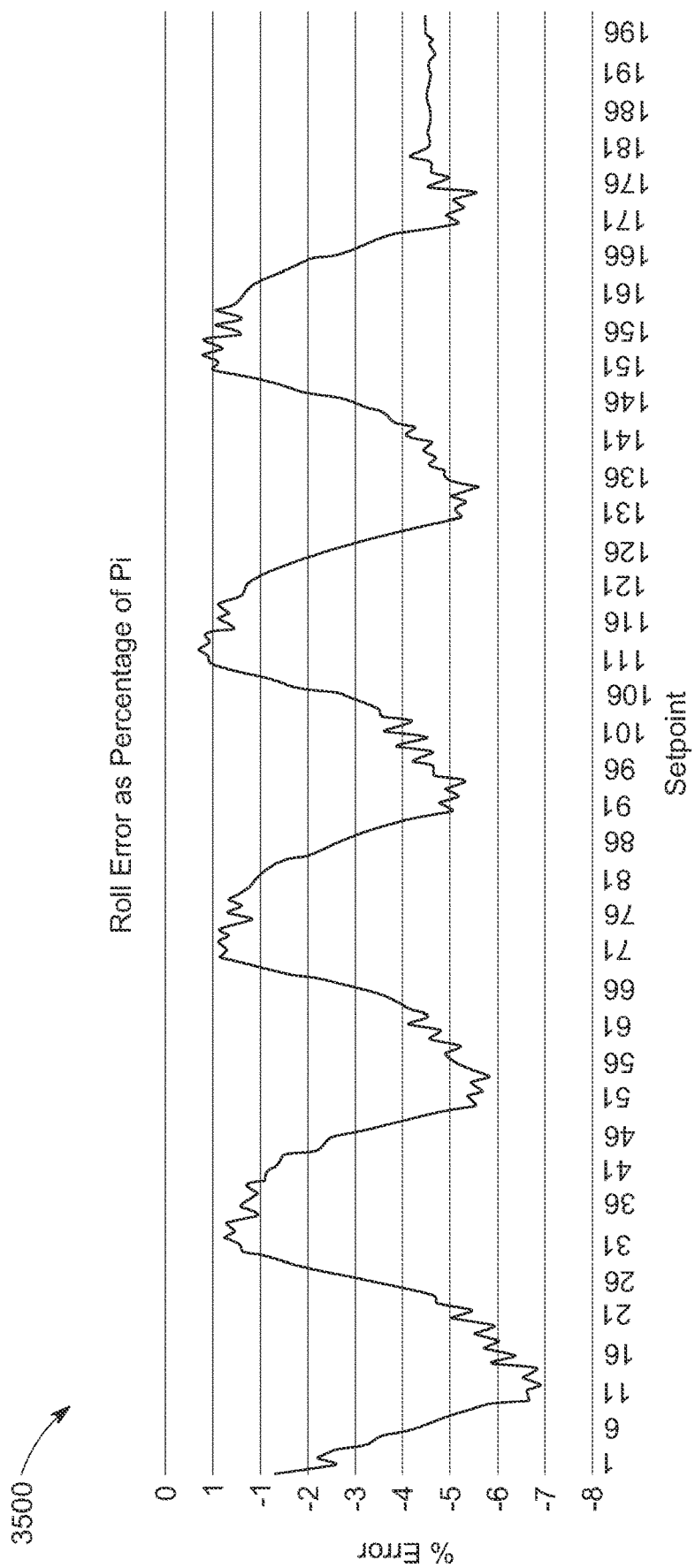
FIG. 35 is a graph showing roll orientation test error in experiments performed on embodiments of the therapeutic social robot.
Figure 36:
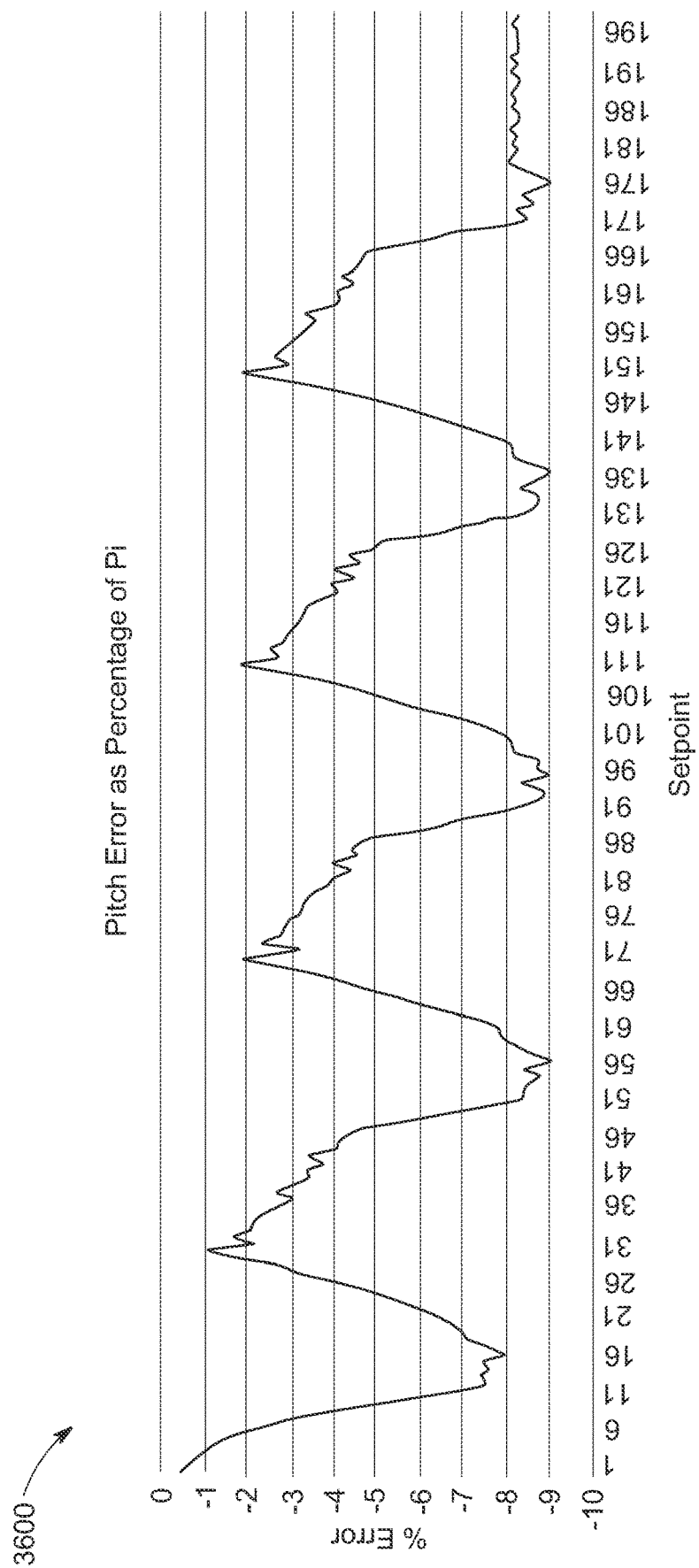
FIG. 36 is a graph showing pitch orientation test error in experiments performed on embodiments of the therapeutic social robot.

For positive roll goal rotations, there is a maximum error of −7% and for pitch there is a maximum error of −9% also occurring at negative goal orientations. When examining the error graphs 3500, 3600 for pitch and roll, FIG. 35 & FIG. 36, toward the end of the trajectory it is observed that there is a static error of around −4.5% for roll orientations and −8% for pitch orientations. The trend line of this offset error is graphed on the orientation graphs as well.

Figure 37:
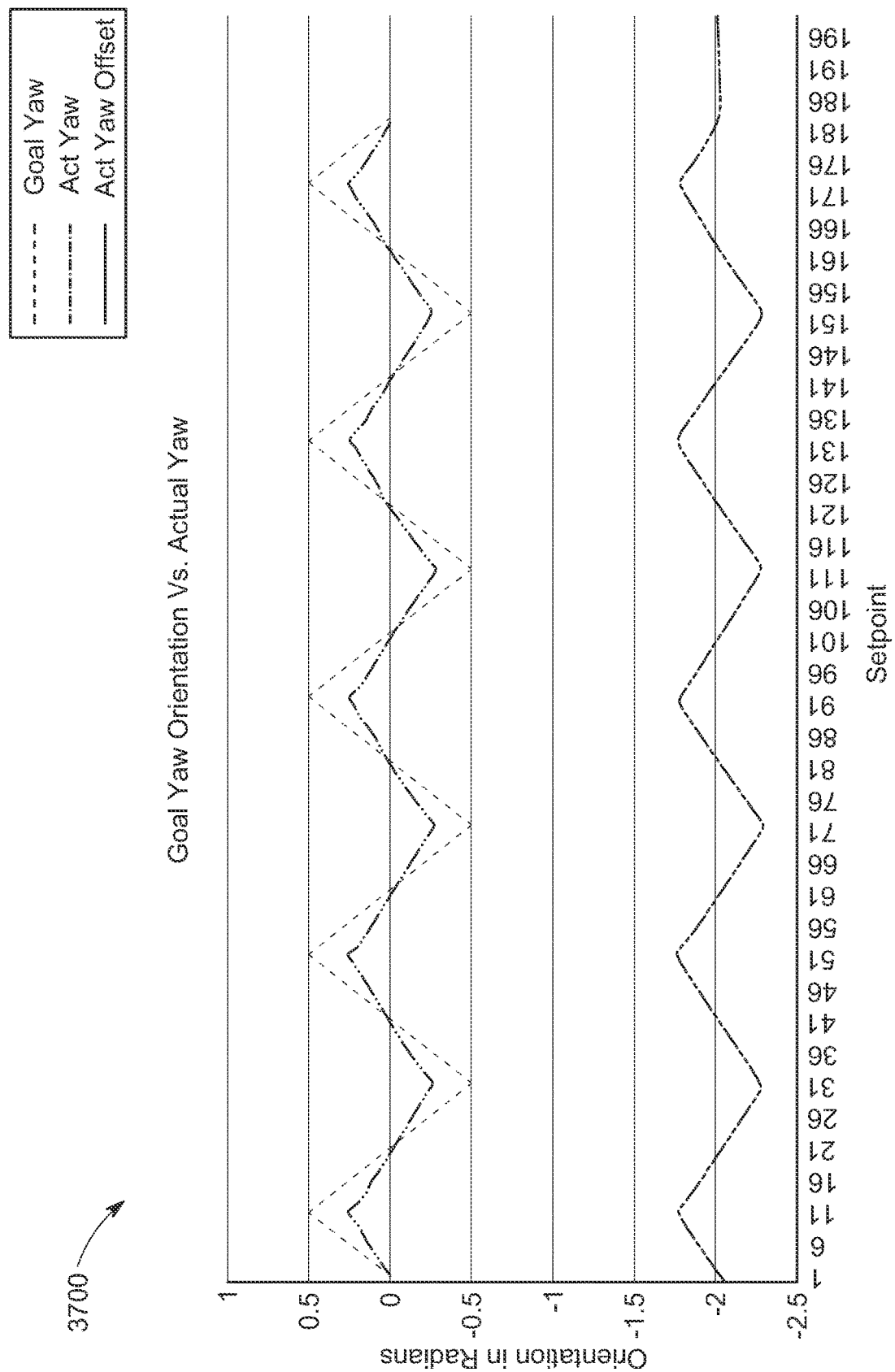
FIG. 37 is a graph showing yaw orientation test results in experiments performed on embodiments of the therapeutic social robot.
Figure 38:
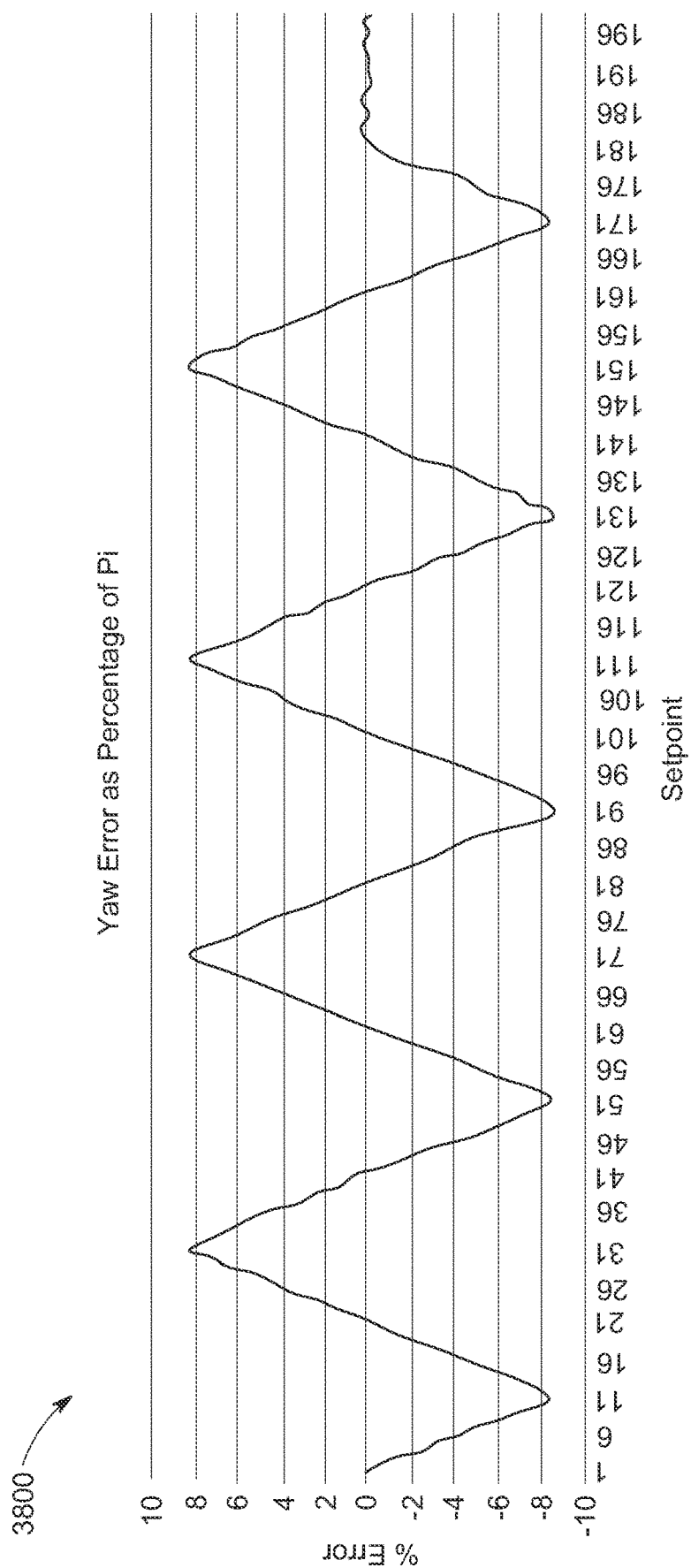
FIG. 38 is a graph showing yaw orientation test error in experiments performed on embodiments of the therapeutic social robot.

When the data for yaw orientations is analyzed, as seen in graph 3700 of FIG. 37, it is observed that the goal position in yaw is never reached, but instead that there is a consistent gap between the actual and goal rotations. This is observed in the error plots 3800, FIG. 38, as an oscillation in position error between ±8% corresponding to negative and positive set points. When the 0 rotation goal stream is sent at the end of the test, there is no cumulative static error indicating that the system returned to home position.

From the tests for roll and pitch orientations, it is tempting to say that the kinematic equation models the system poorly when the goal orientation angles are positive. However, when the yaw data is observed, it is obvious that the amplitude of the actual position does not match the amplitude of the goal position, and that the error between the two increases in direct proportion to the magnitude of rotation angle increase.

When this observation is noted, it also becomes apparent in the rotations about X and Y. The difference being that rotations about X and Y oscillate about their accumulated position error as evidenced by the error graphs in FIG. 35 and FIG. 36. Over 4.5 oscillations, roll motions accrued an error of −4.5%, while the pitch motions had a cumulative error of −8%. Although, it should be noted that the roll and pitch orientations start with error due to initial hemisphere positioning. About X this error is −1.4% and about Y it is 0.47%, however, this does not explain the rapid accumulation of error. Yaw rotations do not show an initial error due to the offset method described in the procedures. Nor do these rotations demonstrate an accrued error over the testing period. In all cases, the error peaks at the extremes of the goal orientation trajectories. In yaw this is clear, but in pitch and roll is only apparent when the oscillations are observed over the error trend line in FIG. 33 and FIG. 34. If these error trend lines are taken as the reference point of the oscillations then the deficit in amplitude is clearer.

When observing the tests visually it is clear that the cumulative error present in roll and pitch motions is due to slip between the omni-wheels and the hemisphere. Because the ballast in the sphere is not mounted in the center, but slightly lower, the center of gravity of the sphere changes in certain orientations. As the mechanism approaches the positive extremes of the trajectory the center of mass of the ball is furthest away from the motors that control its position the most. This causes slip on the omni-wheel that influences the orientation the most, resulting in significant undershoot. When returning to 0 and heading toward negative orientation angles, this undershoot compensates for the smaller amplitude of the motion, causing the error for negative positions to be very low. At negative positions the mass of the ballast is over the most influential motor and does not slip out of static friction. In yaw, this is not an issue as the center of mass of the hemisphere does not change.

The testing conducted demonstrates the viability of the parallel equivalent manipulator kinematics developed for control of the Omni-wheel Base. From the data we can see reasonable position tracking, and quantitatively the motions are expected when observed visually.

In sum, each aspect of the social robot of the present disclosure, starting with the neck & head and finalizing with the Omni-wheel base, is designed to meet the needs of children with ASD. The head was designed to omit the mouth and to be aesthetically pleasing. The neck is then designed to move the head with smooth natural motion. From there the body design is adapted to fit the changes of neck. Further, each mechanical and software component has been designed to allow low-cost manufacturing and easy programming so the social robot may be effectively used in future RAT studies for children with ASD.

Figure 39:
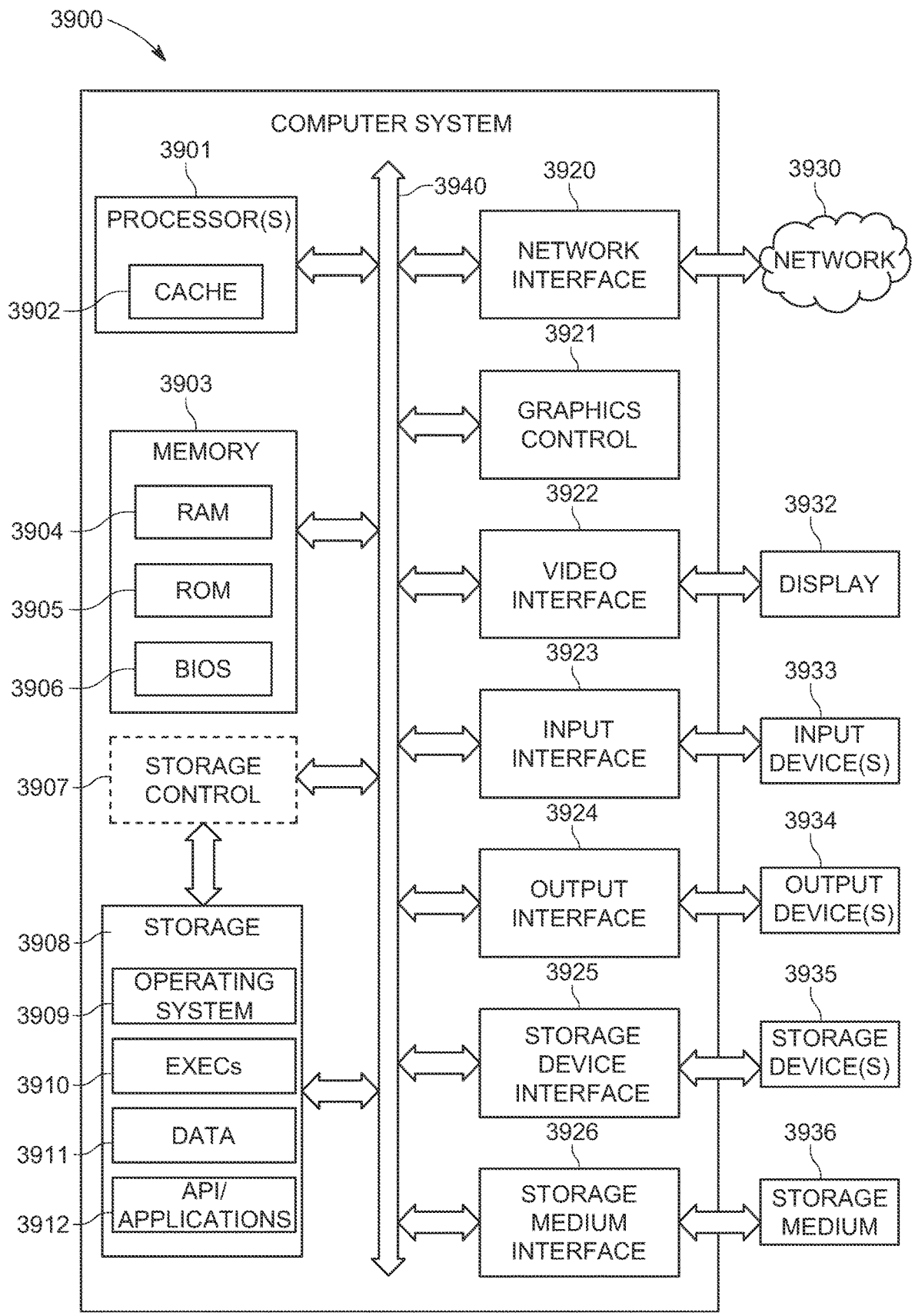
FIG. 39 is a diagram of a computer that may be used to implement one or more aspects of the present disclosure.

Referring next to FIG. 39 it is a block diagram depicting an exemplary machine that includes a computer system 3900 within which a set of instructions can execute for causing a device to perform or execute any one or more of the aspects and/or methodologies of the present disclosure. Embodiments of the disclosure may implement multiple computer systems 3900. The components in FIG. 39 are examples only and do not limit the scope of use or functionality of any hardware, software, embedded logic component, or a combination of two or more such components implementing particular embodiments.

Computer system 3900 may include one or multiple processors 3901, a memory 3903, and a storage 3908 that communicate with each other, and with other components, via a bus 3940. The bus 3940 may also link a display 3932, one or more input devices 3933 (which may, for example, include a keypad, a keyboard, a mouse, a stylus, etc.), one or more output devices 3934, one or more storage devices 3935, and various tangible storage media 3936. All of these elements may interface directly or via one or more interfaces or adaptors to the bus 3940. For instance, the various tangible storage media 3936 can interface with the bus 3940 via storage medium interface 3926. Computer system 3900 may have any suitable physical form, including but not limited to one or more integrated circuits (ICs), printed circuit boards (PCBs), mobile handheld devices (such as mobile telephones or PDAs), laptop or notebook computers, distributed computer systems, computing grids, or servers.

Processor(s) 3901 (or central processing unit(s) (CPU(s))) optionally contains a cache memory unit 3902 for temporary local storage of instructions, data, or computer addresses. Processor(s) 3901 are configured to assist in execution of computer readable instructions. Computer system 3900 may provide functionality for the components depicted in FIG. 1 as a result of the processor(s) 3901 executing non-transitory, processor-executable instructions embodied in one or more tangible computer-readable storage media, such as memory 3903, storage 3908, storage devices 3935, and/or storage medium 3936. The computer-readable media may store software that implements particular embodiments, and processor(s) 3901 may execute the software. Memory 3903 may read the software from one or more other computer-readable media (such as mass storage device(s) 3935, 3936) or from one or more other sources through a suitable interface, such as network interface 3920. The software may cause processor(s) 3901 to carry out one or more processes or one or more steps of one or more processes described or illustrated herein. Carrying out such processes or steps may include defining data structures stored in memory 3903 and modifying the data structures as directed by the software.

The memory 3903 may include various components (e.g., machine readable media) including, but not limited to, a random access memory component (e.g., RAM 3904) (e.g., a static RAM "SRAM", a dynamic RAM "DRAM, etc.), a read-only component (e.g., ROM 3905), and any combinations thereof. ROM 3905 may act to communicate data and instructions unidirectionally to processor(s) 3901, and RAM 3904 may act to communicate data and instructions bidirectionally with processor(s) 3901. ROM 3905 and RAM 3904 may include any suitable tangible computer-readable media described below. In one example, a basic input/output system 3906 (BIOS), including basic routines that help to transfer information between elements within computer system 3900, such as during start-up, may be stored in the memory 3903.

Fixed storage 3908 is connected bidirectionally to processor(s) 3901, optionally through storage control unit 3907. Fixed storage 3908 provides additional data storage capacity and may also include any suitable tangible computer-readable media described herein. Storage 3908 may be used to store operating system 3909, EXECs 3910 (executables), data 3911, API applications 3912 (application programs), and the like. Often, although not always, storage 3908 is a secondary storage medium (such as a hard disk) that is slower than primary storage (e.g., memory 3903). Storage 3908 can also include an optical disk drive, a solid-state memory device (e.g., flash-based systems), or a combination of any of the above. Information in storage 3908 may, in appropriate cases, be incorporated as virtual memory in memory 3903.

In one example, storage device(s) 3935 may be removably interfaced with computer system 3900 (e.g., via an external port connector (not shown)) via a storage device interface 3925. Particularly, storage device(s) 3935 and an associated machine-readable medium may provide nonvolatile and/or volatile storage of machine-readable instructions, data structures, program modules, and/or other data for the computer system 3900. In one example, software may reside, completely or partially, within a machine-readable medium on storage device(s) 3935. In another example, software may reside, completely or partially, within processor(s) 3901.

Bus 3940 connects a wide variety of subsystems. Herein, reference to a bus may encompass one or more digital signal lines serving a common function, where appropriate. Bus 3940 may be any of several types of bus structures including, but not limited to, a memory bus, a memory controller, a peripheral bus, a local bus, and any combinations thereof, using any of a variety of bus architectures. As an example, and not by way of limitation, such architectures include an Industry Standard Architecture (ISA) bus, an Enhanced ISA (EISA) bus, a Micro Channel Architecture (MCA) bus, a Video Electronics Standards Association local bus (VLB), a Peripheral Component Interconnect (PCI) bus, a PCI-Express (PCI-X) bus, an Accelerated Graphics Port (AGP) bus, HyperTransport (HTX) bus, serial advanced technology attachment (SATA) bus, and any combinations thereof.

Computer system 3900 may also include an input device 3933. In one example, a user of computer system 3900 may enter commands and/or other information into computer system 3900 via input device(s) 3933. Examples of an input device(s) 3933 include, but are not limited to, an alpha-numeric input device (e.g., a keyboard), a pointing device (e.g., a mouse or touchpad), a touchpad, a joystick, a gamepad, an audio input device (e.g., a microphone, a voice response system, etc.), an optical scanner, a video or still image capture device (e.g., a camera), and any combinations thereof. Input device(s) 3933 may be interfaced to bus 3940 via any of a variety of input interfaces 3923 (e.g., input interface 3923) including, but not limited to, serial, parallel, game port, USB, FIREWIRE, THUNDERBOLT, or any combination of the above.

In particular embodiments, when computer system 3900 is connected to network 3930, computer system 3900 may communicate with other devices, specifically mobile devices and enterprise systems, connected to network 3930. Communications to and from computer system 3900 may be sent through network interface 3920. For example, network interface 3920 may receive incoming communications (such as requests or responses from other devices) in the form of one or more packets (such as Internet Protocol (IP) packets) from network 3930, and computer system 3900 may store the incoming communications in memory 3903 for processing. Computer system 3900 may similarly store outgoing communications (such as requests or responses to other devices) in the form of one or more packets in memory 3903 and communicated to network 3930 from network interface 3920. Processor(s) 3901 may access these communication packets stored in memory 3903 for processing.

Examples of the network interface 3920 include, but are not limited to, a network interface card, a modem, and any combination thereof. Examples of a network 3930 or network segment 3930 include, but are not limited to, a wide area network (WAN) (e.g., the Internet, an enterprise network), a local area network (LAN) (e.g., a network associated with an office, a building, a campus or other relatively small geographic space), a telephone network, a direct connection between two computing devices, and any combinations thereof. A network, such as network 3930, may employ a wired and/or a wireless mode of communication. In general, any network topology may be used.

Information and data can be displayed through a display 3932. Examples of a display 3932 include, but are not limited to, a liquid crystal display (LCD), an organic liquid crystal display (OLED), a cathode ray tube (CRT), a plasma display, and any combinations thereof. The display 3932 can interface to the processor(s) 3901, memory 3903, and fixed storage 3908, as well as other devices, such as input device(s) 3933, via the bus 3940. The display 3932 is linked to the bus 3940 via a video interface 3922, and transport of data between the display 3932 and the bus 3940 can be controlled via the graphics control 3921.

In addition to a display 3932, computer system 3900 may include one or more other peripheral output devices 3934 including, but not limited to, an audio speaker, a printer, and any combinations thereof. Such peripheral output devices may be connected to the bus 3940 via an output interface 3924. Examples of an output interface 3924 include, but are not limited to, a serial port, a parallel connection, a USB port, a FIREWIRE port, a THUNDERBOLT port, and any combinations thereof.

In addition, or as an alternative, computer system 3900 may provide functionality as a result of logic hardwired or otherwise embodied in a circuit, which may operate in place of or together with software to execute one or more processes or one or more steps of one or more processes described or illustrated herein. Reference to software in this disclosure may encompass logic, and reference to logic may encompass software. Moreover, reference to a computer-readable medium may encompass a circuit (such as an IC) storing software for execution, a circuit embodying logic for execution, or both, where appropriate. The present disclosure encompasses any suitable combination of hardware, software, or both.

Those of skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A therapeutic system comprising:
    a posture-mimicry robot assembly comprising:
        a head assembly;
        a neck assembly positioned below and affixed to the head assembly, the neck assembly comprising at least one actuator positioned within the neck assembly and configured to adjust an angular position of the head assembly relative to the neck assembly;
        a body assembly positioned below and affixed to the neck assembly, the body assembly comprising:
            a plurality of support structures configured to affix the neck assembly to the body assembly and form a torso, and
            a hemispherical bottom portion positioned beneath the torso;
        one or more transducers configured to detect audio signals from a subject and emit audio signals from an operator;
        one or more visual input components configured to detect movement of the subject and transmit the detected movement via visual input signals;
    a base assembly comprising:
        a reinforcement structure defining a top surface,
        a receiving aperture configured to receive the hemispherical bottom portion of the body assembly, and
        three or more rotary actuators configured to engage with a curved surface of the hemispherical bottom portion of the body assembly, wherein the three or more rotary actuators are configured to adjust an angular position of the hemispherical bottom portion of the body assembly relative to the base assembly; and
    a controller configured to receive and transmit audio signals from the operator to the transducer and configured to facilitate posture-mimicry of the subject through adjusting an angular position of the head assembly through the at least one actuator of the neck assembly and by adjusting an angular position of the hemispherical bottom portion of the body assembly through the at least three rotary actuators of the base assembly.

2. The system of claim 1, further comprising at least one central computing component configured to relay audio input and output signals and visual input and output signals to and from the posture-mimicry robot assembly via command signals to and from the controller and the operator.

3. The system of claim 1, wherein the one or more visual input components is a full-body skeletal tracking system configured to detect movement from the subject, isolate the subject's head and torso from the movement, and transmit visual input signals to the controller to enable posture-mimicry of the subject.

4. The system of claim 1, wherein the one or more visual input components are one or more cameras, wherein the one or more cameras are configured to detect movement of the subject's head and torso, isolate the subject's gaze and posture, and transmit visual input signals to the controller to center the head assembly of the posture-mimicry robot with the subject's gaze, and effectuate posture-mimicry of the subject.

5. The system of claim 1, wherein the head assembly further comprises a display configured to display emotive actions via eyes and/or other facial elements.

6. A non-transitory, tangible processor readable storage medium, encoded with processor readable instructions to perform therapeutic interactive movements, gestures, and audio-visual cues, to imitate a posture of a subject through a posture-mimicry robot assembly, the instructions comprising instructions to:
- detect, at least, movement of a subject through one or more visual input components;
- process the detected movement to generate actuator control signals and command signals; and
- initiate, using the actuator control signals and the command signals, imitation of the subject's posture by the posture-mimicry robot assembly by:
  - adjusting, via a controller, an angular position of a head assembly of the posture-mimicry robot assembly to imitate or exaggerate an angular position of the subject's head;
  - adjusting, via the controller, an angular position of a hemispherical bottom portion of the posture-mimicry robot assembly to imitate or exaggerate an angular position of the subject's body; and
  - emit auditory and visual cues to the subject.

7. The non-transitory, tangible processor readable storage medium of claim 6 wherein the adjusting of the angular position of the head assembly is accomplished by at least one rotary actuator in a neck assembly affixed to the head assembly.

8. The non-transitory, tangible processor readable storage medium of claim 7, wherein the head assembly further comprises a display configured to display emotive actions via eyes and/or other facial elements.

9. The non-transitory, tangible processor readable storage medium of claim 6, wherein the adjusting of the angular position of the hemispherical bottom portion of the posture-mimicry robot assembly is accomplished three or more rotary actuators in a base assembly.

10. The non-transitory, tangible processor readable storage medium of claim 9, wherein the adjusting of the hemispherical bottom portion of the posture-mimicry robot assembly is further directed by a PID controller, a deep neural network, and a PID algorithm.

11. The non-transitory, tangible processor readable storage medium of claim 6, wherein at least one central computing component is configured to relay audio input and output signals and visual input and output signals to and from the posture-mimicry robot assembly via command signals to and from a controller and an operator.

12. The non-transitory, tangible processor readable storage medium of claim 6, wherein the detecting is accomplished by a full-body skeletal tracking system configured to detect movement from the subject, isolate the subject's head and torso from the movement, and transmit visual input signals to the controller to effectuate posture-mimicry of the subject.

13. The non-transitory, tangible processor readable storage medium of claim 6, wherein the detecting is accomplished by one or more cameras, wherein the one or more cameras are configured to detect movement of the subject's head and torso, isolate the subject's gaze and posture, and transmit visual input signals to the controller to center the head assembly of the posture-mimicry robot with the subject's gaze, and effectuate posture-mimicry of the subject.

14. A method for performing therapeutic interactive movements, gestures, and audio-visual cues, to imitate a posture of a subject through a posture-mimicry robot assembly, the method comprising:
- detecting, via one or more visual input components, movement of a subject;
- transmitting, in response to the detected movement of the subject, an actuator control signal;
- processing, via a central computing component, the detected movement to generate a command signal;
- transmitting, via the central computing component, the command signal; and
- processing the command signal, via a controller, to initiate posture imitation of the subject by the posture-mimicry robot assembly, wherein the posture imitation comprises:
  - engaging, via the controller, three or more rotary actuators comprising at least three serial link manipulators, each of the serial link manipulators operating with three intersecting degrees of freedom;
  - rotating one or more of the three or more rotary actuators, wherein a rotational movement of each of the three or more rotary actuators is defined by an axis that is coincident with a center of a hemispherical bottom portion of the posture-mimicry robot assembly;
  - adjusting, via the three or more rotary actuators, an angular position of the hemispherical bottom portion of the posture-mimicry robot assembly to imitate or exaggerate an angular position of a subject's body as detected by the one or more visual input components; and
  - emitting, via one or more transducers, audible transmission to the subject.

15. The method of claim 14 further comprising the step of:
- adjusting, via at least one rotary actuator in a neck assembly of the posture-mimicry robot assembly, an angular position of a head assembly of the posture-mimicry robot assembly in response to movement of the subject's head as detected by the one or more visual input components.

16. The method of claim 15, wherein the head assembly of the posture-mimicry robot further comprises a display configured to display emotive actions via eyes and/or other facial elements.

17. The method of claim 14 further comprising the step of:
- determining an actual position of the three or more rotary actuators using a PID controller and a standard PID algorithm, prior to processing the command signal, wherein an error between a desired and an actual position is calculated with an integral and a derivative of the error, each modified by their respective gains.

18. The method of claim 14, wherein the emitted audible transmission are relayed to the subject, via the one or more transducers, by one of an operator or pre-programmed response.

19. The method of claim 14, wherein the transmitting of the actuator control signal is directed by an operator.

20. The method of claim 14, wherein the transmitting of the actuator control signal is directed by an autonomous artificial intelligence model configured to elicit behavioral responses from the subject.

* * * * *